(12) United States Patent
Kashima et al.

(10) Patent No.: US 6,884,997 B2
(45) Date of Patent: Apr. 26, 2005

(54) METHOD AND APPARATUS FOR DETECTING DANGEROUS SUBSTANCES AND SUBSTANCES OF INTEREST

(75) Inventors: Hideo Kashima, Kokubunji (JP); Izumi Waki, Asaka (JP); Yasuaki Takada, Kiyose (JP); Hisashi Nagano, Hachioji (JP); Katsumi Nagumo, Yokohama (JP); Mitsuhiro Noda, Fujisawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/391,630

(22) Filed: Mar. 20, 2003

(65) Prior Publication Data

US 2004/0124352 A1 Jul. 1, 2004

(30) Foreign Application Priority Data

Dec. 27, 2002 (JP) .................................. 2002-378948

(51) Int. Cl.[7] .......................... H01J 49/04; H01J 39/34; B01D 59/54
(52) U.S. Cl. ...................... 250/288; 250/281; 250/282; 250/287; 250/324; 250/423 P; 250/423 R; 250/424; 250/425; 250/440.11; 250/442.11; 436/43; 436/48; 436/104; 436/156; 436/157
(58) Field of Search ................................ 250/281, 282, 250/288, 287, 324, 423 P, 424, 423 R, 425, 440.11, 442.11, 440.1, 423, 288 A; 436/43, 48, 104, 156, 157

(56) References Cited

U.S. PATENT DOCUMENTS

| | | | | |
|---|---|---|---|---|
| 4,075,475 A | * | 2/1978 | Risby et al. ................ | 250/282 |
| 4,820,920 A | * | 4/1989 | Bather ....................... | 250/282 |
| 5,382,793 A | * | 1/1995 | Weinberger et al. ....... | 250/288 |
| 5,405,781 A | | 4/1995 | Davies et al. | |
| 5,594,243 A | * | 1/1997 | Weinberger et al. ....... | 250/288 |
| 5,663,561 A | | 9/1997 | Franzen et al. | |
| 5,741,984 A | | 4/1998 | Danylewych-May et al. | |
| 5,789,256 A | * | 8/1998 | Marlow et al. ............. | 436/156 |
| 5,918,254 A | * | 6/1999 | Bottiger et al. ............. | 73/1.06 |
| 6,053,059 A | | 4/2000 | Muranaka et al. | |
| 6,225,623 B1 | | 5/2001 | Turner et al. | |
| 6,403,329 B1 | * | 6/2002 | Novak et al. ................ | 435/20 |
| 6,420,181 B1 | * | 7/2002 | Novak ....................... | 436/104 |
| 6,483,108 B1 | * | 11/2002 | Sakairi ....................... | 250/288 |
| 6,631,333 B1 | * | 10/2003 | Lewis et al. ................. | 702/24 |
| 6,649,910 B2 | * | 11/2003 | Sakairi ....................... | 250/288 |
| 2002/0060288 A1 | * | 5/2002 | Hughey et al. ............. | 250/281 |
| 2002/0066857 A1 | * | 6/2002 | Hughey et al. ............. | 250/281 |
| 2003/0020013 A1 | * | 1/2003 | Sakairi ....................... | 250/288 |
| 2003/0064520 A1 | * | 4/2003 | Hiatt .......................... | 436/43 |
| 2003/0153021 A1 | * | 8/2003 | Lu et al. .................... | 435/7.32 |
| 2003/0157564 A1 | * | 8/2003 | Smith et al. ................ | 435/7.1 |
| 2003/0197121 A1 | * | 10/2003 | Turecek et al. ............. | 250/281 |
| 2004/0124352 A1 | * | 7/2004 | Kashima et al. ........... | 250/288 |

FOREIGN PATENT DOCUMENTS

GB 2 363 517 A 12/2001

* cited by examiner

Primary Examiner—John R. Lee
Assistant Examiner—Bernard E. Souw
(74) Attorney, Agent, or Firm—Antonelli, Terry, Stout & Kraus, LLP

(57) ABSTRACT

A dangerous substance detecting apparatus comprises an oven for accommodating a wiping member stuck with a sample derived from a dangerous substance, a light source for emitting infrared rays for heating the sample, an ion source for ionizing the sample evaporated in the oven, a mass analyzer for performing a mass analysis on ions, a data processing unit for processing an output signal from the mass analyzer to determine the presence or absence of a dangerous substance, an operation panel for displaying the result of the determination, an alarm unit for generating an alarm based on the result of the determination, and a control unit for controlling the respective components of the apparatus based on operating conditions entered from the operation panel and specified for the respective components of the apparatus.

28 Claims, 15 Drawing Sheets

METHOD AND APPARATUS FOR DETECTING DANGEROUS SUBSTANCES AND SUBSTANCES OF INTEREST

BACKGROUND OF THE INVENTION

The present invention relates to dangerous substance detecting techniques based on the mass spectrometry, and more particularly, to a method and apparatus for detecting a dangerous substance.

JP-A-2000-028579 and JP-A-2001-093461 propose dangerous substance detecting techniques based on the mass spectrometry which basically excel in the speed, sensitivity and selectivity. U.S. Pat. No. 4,909,090 in turn proposes a vapor sampling probe which has a lamp disposed on the front face for heating the surface of a sample in an object under testing.

A dangerous substance detecting apparatus is required to rapidly determine in case of emergency, for example, when a suspicious article is detected, whether or not the suspicious article includes an explosive dangerous substance. In addition, the dangerous substance detecting apparatus is desirably capable of highly selectively detecting a trace of marks at a high sensitivity. A testing of infinitesimal marks at a high sensitivity involves efficiently feeding the marks to an ion source for ionization and performing a mass analysis using a mass spectrometer. Also desirably, the dangerous substance detecting apparatus is portable so that it can be carried anywhere with a high mobility, and can be driven with low power consumption.

SUMMARY OF THE INVENTION

The present invention is intended to address the following challenges.

(1) A sample extracted from an object under testing is evaporated in a short time in a high concentration, and the evaporated sample is introduced into an ion source unit for ionization to enhance the detection sensitivity.

(2) A reduction is achieved in the maximum power consumption required to drive a dangerous substance detecting apparatus.

(3) The dangerous substance detecting apparatus is improved in mobility.

(4) A wiping member stuck with a sample extracted from an object under testing by wiping is carried into the dangerous substance detecting apparatus with ease to improve the operability and performance of the apparatus.

(5) An atmospheric ion source is integrated with a test slip receiver which is loaded with the wiping member stuck with a sample extracted from an object under testing by wiping to improve the operability and performance of the dangerous substance detecting apparatus.

It is an object of the present invention to provide a method and apparatus for detecting a dangerous substance which is capable of detecting a dangerous substance at a high sensitivity with a good operability.

In a dangerous substance detecting apparatus according to the present invention, a clean wiping member for collecting a sample is used to collect, through wiping, particles stuck on an object under testing such as clothing, bag and the like, and the particles are used as a test sample. The wiping member used herein may be a test slip made of a soft material such as cloth, filter paper or the like. However, the test slip is not limited to such material as cloth and paper, but may be made of a porous polymer. The wiping member, which is stuck with a sample derived from a dangerous substance, is accommodated in a chamber which comprises a resistive heating means, where the surface of the wiping member stuck with the sample is exposed. The sample derived from a dangerous substance includes products decomposed from the dangerous substance as well as the dangerous substance itself. A light source for emitting infrared rays having a maximum energy distribution in a wavelength band from 0.7 $\mu$m to 2 $\mu$m is used to heat, with the infrared rays, the surface stuck with the sample of the wiping member accommodated in the chamber. The sample stuck on the wiping member is heated by the infrared rays, and is evaporated. Instead of the heating with the infrared rays, heated air generated by an air heat source may be sucked into the chamber for heating the wiping member to evaporate the sample. An ion source unit is connected to the chamber in which the evaporated sample is ionized, and a mass analysis unit performs a mass analysis on resulting ions. The dangerous substance detecting apparatus according to the present invention can heat the sample to high temperatures in a short time using the infrared rays or heated air, and generate the evaporated sample in a high concentration in a short time to improve the detection sensitivity for a dangerous substance.

The dangerous substance detecting apparatus according to the present invention can sequentially heat the sample in steps by supplying the light source for emitting infrared rays with the power which sequentially varies from a lower value to a higher value. Therefore, when a plurality of kinds of samples, derived from dangerous substances, are collected by the wiping member, in other words, when a plurality of dangerous substances or products decomposed from the dangerous substances exist on the wiping member, the samples can be selectively evaporated on a kind-by-kind basis in accordance with the temperatures to which the heated wiping member reaches, thereby improving the detection sensitivity for the dangerous substances and the selectivity for the dangerous substances to be detected.

In the dangerous substance detecting apparatus according to the present invention, since the heating means for heating the chamber is powered off while the light source for emitting infrared rays or the air heat source is powered on, dangerous substances can be efficiently sensed without increasing the overall power consumption of the apparatus.

The dangerous substance detecting apparatus according to the present invention includes conveyer means for conveying the wiping member from the outside of the chamber to the interior of the chamber. A sample stuck on the wiping member conveyed into the chamber is automatically tested, and after the test, the wiping member is automatically discarded into a dust box. The components of the apparatus associated with the test are automatically controlled to avoid participation of the operator in the control.

The dangerous substance detecting apparatus according to the present invention includes a sample base (holder member) for holding the wiping member, a cassette for accommodating a plurality of sample bases, and conveyer means for conveying the sample base from the cassette into the chamber, or conveyer means for collectively conveying the cassette into the chamber. Therefore, a plurality of wiping members can be automatically conveyed one by one into the chamber, or a plurality of wiping members can be collectively conveyed into the chamber to test samples stuck on the respective wiping members one by one or to collectively test the samples stuck on the plurality of wiping members.

The dangerous substance detecting apparatus according to the present invention includes an atmospheric ion source unit having a corona discharge section, a wiping member receiver for receiving a wiping member which has a sample stuck thereon, collected from an object under testing through wiping, and a housing configured to integrate the atmospheric ion source unit with the wiping member receiver. The wiping member receiver has an opening in an upper portion or a lateral portion thereof, so that the wiping member is inserted into the wiping member receiver from the opening formed in the upper or lateral portion. The housing is heated by first heating means through resistive heating. An optical window is provided on a side wall of the wiping member receiver. A side wall or a region including the side wall of the wiping member receiver is made movable. The surface of the wiping member, on which the sample is stuck, inserted into the wiping member receiver is heated by second heating means through irradiation of infrared rays via the optical window. Instead of the optical window provided on the side wall of the wiping member receiver, the second heating means relying on the irradiation of infrared rays may be disposed in a hole formed in a side wall of the wiping member receiver to heat the surface of the wiping member, on which a sample is stuck, inserted into the wiping member receiver. The sample evaporated in the wiping member receiver is sent back to the corona discharge section by a gas which flows from the wiping member receiver through a filter. Ions of the sample generated in the corona discharge section are supplied to a mass analysis unit for a mass analysis. The dangerous substance detecting apparatus determines the presence or absence of a dangerous substance included in the sample collected from the object under testing based on the result of the mass analysis on the ions of the sample. Then, the apparatus reads a database which includes mass spectrographic data on dangerous substances stored in storage means, and compares the database with the result of the mass analysis on the ions of the sample to determine the presence or absence of a dangerous substance included in the sample. The result of the comparison is displayed on display means.

In another aspect, a method of detecting a dangerous substance according to the present invention includes the steps of accommodating a wiping member in a chamber so as to expose a surface stuck with a sample collected from an object under testing through wiping, for evaporation of the sample, heating the chamber by first heating means through resistive heating, heating the surface of the wiping member on which the sample is stuck by second heating means using infrared rays through an optical window from the outside of the chamber to evaporate the sample, ionizing the evaporated sample, performing a mass analysis on ions of the sample, and determining the presence or absence of a dangerous substance included in the sample based on the result of the mass analysis made on the ions of the sample.

In the method of detecting a dangerous substance described above, power is alternately supplied to the first heating means and to the second heating means.

The power may be supplied to the second heating means in steps.

The method of detecting a dangerous substance described above further includes the step of removing the wiping member from the chamber, wherein the step of accommodating includes supplying the power to the first heating means, the step of evaporating includes stopping supplying the power to the first heating means and supplying the power to the second heating means, and the step of removing includes supplying the power to the first heating means and stopping supplying the power to the second heating means.

Another method of detecting a dangerous substance according to the present invention includes the steps of inserting a wiping member into a wiping member receiver of a housing configured to integrate an atmospheric ion source unit having a corona discharge section with the wiping member receiver for receiving the wiping member stuck with a sample collected from an object under testing through wiping, heating the housing by first heating means using resistive heating, heating the surface of the wiping member on which the sample is stuck by second heating means using infrared rays to evaporate the sample, flowing a gas from the wiping member receiver to send the sample evaporated in the wiping member receiver back to the corona discharge section, performing a mass analysis on ions of the sample generated in the corona discharge section, and determining the presence or absence of a dangerous substance included in the sample based on the result of the mass analysis on the ions of the sample.

In the method of detecting a dangerous substance described above, power is alternately supplied to the first heating means and to the second heating means.

The power may be supplied to the second heating means in steps.

The method of detecting a dangerous substance described above further includes the step of removing the wiping member from the wiping member receiver, wherein the step of inserting includes supplying the power to the first heating means, the step of evaporating includes stopping supplying the power to the first heating means and supplying the power to the second heating means, and the step of removing includes supplying the power to the first heating means and stopping supplying the power to the second heating means.

Other objects, features and advantages of the invention will become apparent from the following description of the embodiments of the invention taken in conjunction with the accompanying drawings.

DETAILED DESCRIPTION OF THE INVENTION

A dangerous substance detecting apparatus according to the present invention can be used in any of a portable form and a stationary form.

In the following, embodiments of the present invention will be described in detail with reference to the accompanying drawings. In the following description of the embodiments, dangerous substances include, for example, explosive materials, medicines such as stimulant drug, chemicals which adversely affect the human body, viomaterials such as bacteria, virus and the like which adversely affect the human body, and other materials which are generally assumed to adversely affect the human body.

The dangerous substance detecting apparatus according to the present invention uses a test sample which includes particles that are stuck on an object under testing and wiped off for sampling by a wiping member represented by a test slip made of a clean and soft material such as cloth and filter paper. The dangerous substance detecting apparatus according to the present invention features that infrared rays are used to heat a surface of the wiping member on which a sample is adhered to evaporate the sample. While the following description will be made on an exemplary apparatus which employs a halogen lamp for a light source for generating infrared rays, the present invention is not limited to the use of the halogen lamp. Instead of the halogen lamp, a heat source which reddens during heating, for example, a ceramic heater may be disposed at a position opposing the surface of the wiping member on which the sample is stuck, to heat the surface of the wiping member through the absorption of the infrared rays and the transfer of radiant heat, resulting in similar effects to those provided by the use of the halogen lamp, as will be later described.

Figure 1:
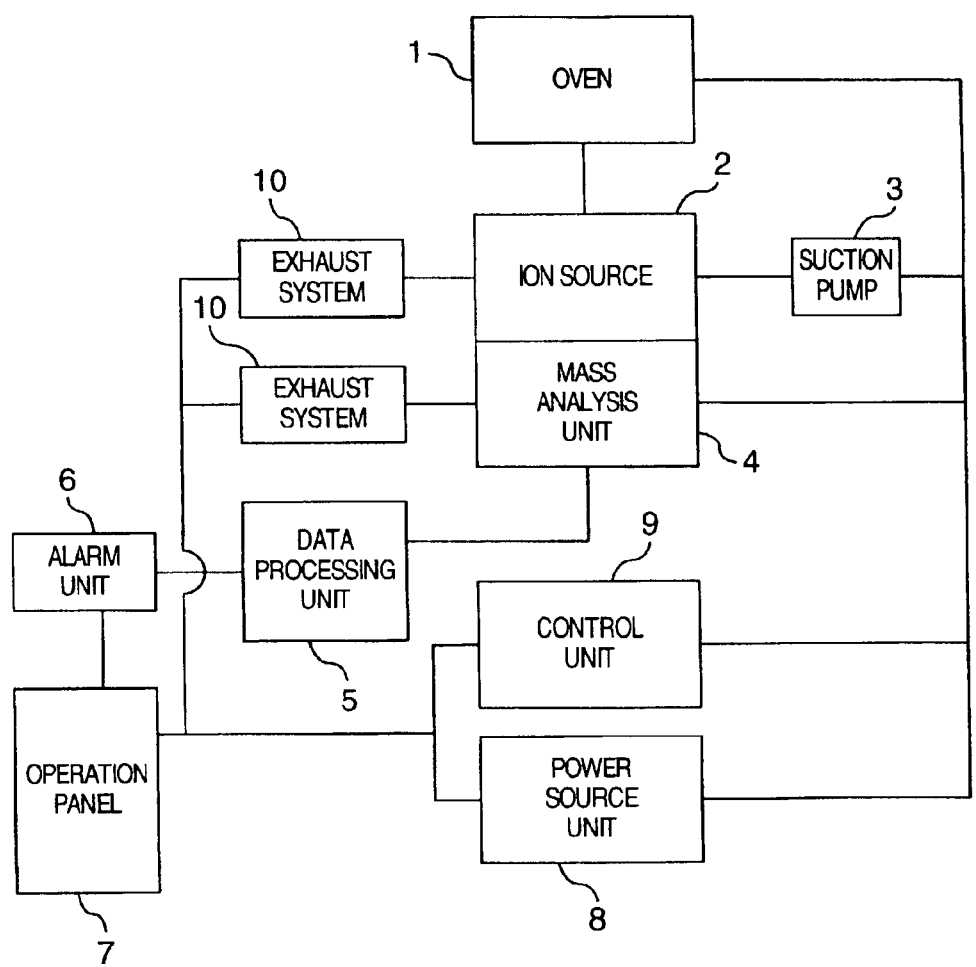
FIG. 1 is a block diagram illustrating the main configuration of a dangerous substance detecting apparatus according to an embodiment of the present invention.

FIG. 1 is a block diagram illustrating the main configuration of the dangerous substance detecting apparatus according to a first embodiment of the present invention.

A sample derived from a dangerous substance is adhered on the wiping member which is placed into an oven 1 to heat the sample. In addition, from the outside of the oven 1, a light source for emitting infrared rays irradiates the surface of the wiping member, on which the sample is stuck, with the infrared rays to heat the sample for evaporation. An ion source unit 2 is connected to the oven 1. The evaporated sample is introduced into the ion source unit 2 by a suction pump 3 for ionization. Ions generated in the ion source unit 2 are applied to a mass analysis unit 4 for a mass analysis. The ion source unit 2 and mass analysis unit 4 are exhausted by an exhaust system 10.

A data processing unit 5 has a storage means which stores a database that includes mass analysis data (the value of m/e and a relative strength, where m is the mass number of ions, and e is the valence of the ions) required for identifying a plurality of dangerous substances. The mass analysis unit 4 comprises a mass spectrometer that includes a detector, the output of which is sent to the data processing unit 5 as the result of the mass analysis on the ions of the sample. The data processing unit 5 performs data processing such as a comparison of the data in the database read from the storage means with the result of the mass analysis on the ions to determine the presence or absence of dangerous substances. The result of the determination on the presence or absence of dangerous substances is displayed on an operation panel 7 or on a display of the data processing unit 5. In addition, based on the result of the determination on the presence or absence of dangerous substances, an alarm may be generated from an alarm unit 6. A control unit 9 controls a power source unit 8 for powering the respective components of the apparatus, and also controls the respective components of the apparatus. Operating conditions specified for the respective components of the apparatus are entered from the operation panel 7, such that the control unit 9 controls the operation of the respective components of the apparatus based on the entered operating conditions.

(First Embodiment)

Figure 2:
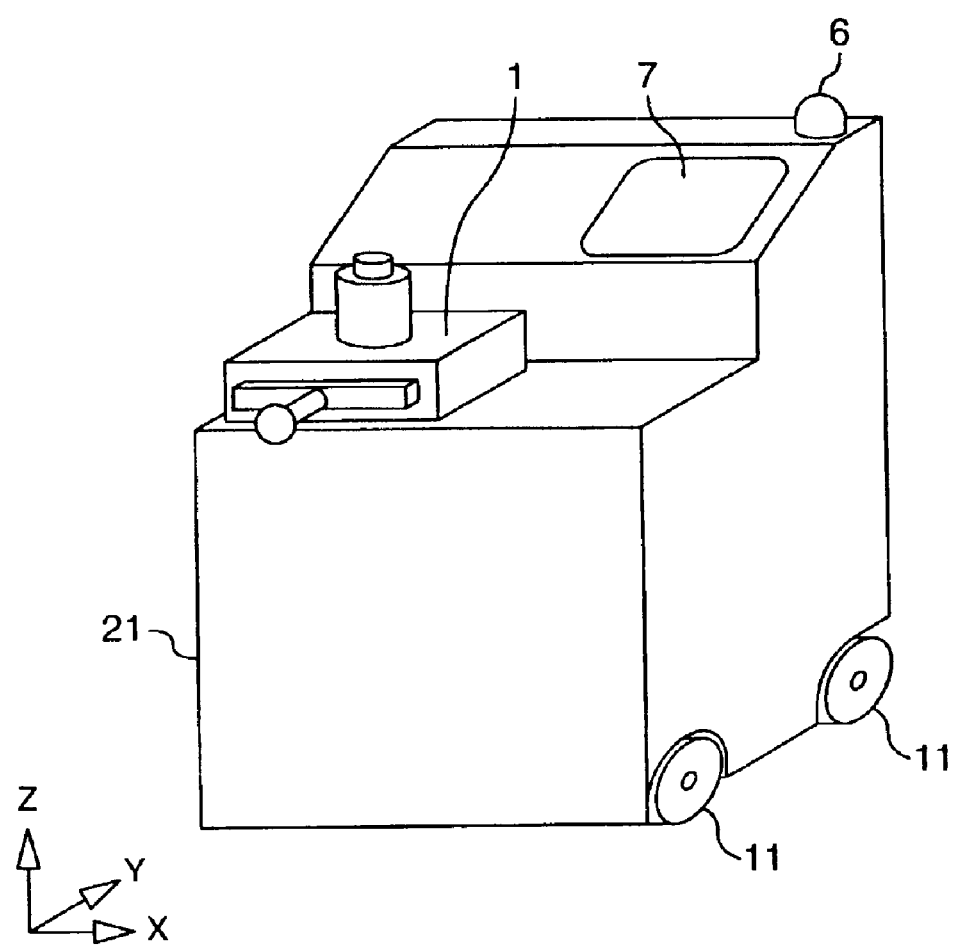
FIG. 2 is a perspective view illustrating the appearance of a dangerous substance detecting apparatus according to a first embodiment of the present invention.

FIG. 2 is a perspective view illustrating the appearance of a portable dangerous substance detecting apparatus according to a first embodiment of the present invention. A cover 23 for covering the oven 1 is omitted in FIG. 2. The components illustrated in FIG. 1 except for the oven 1, alarm unit 6 and operation panel 7 are contained in a housing 21 of the apparatus illustrated in FIG. 2. The apparatus is provided with wheels 11 for facilitating its movements. Relative positioning of the oven 1, alarm unit 6 and operation panel 7 to one another can be changed as required depending on a particular manner of carrying the wiping member into the oven 1.

Figure 3:
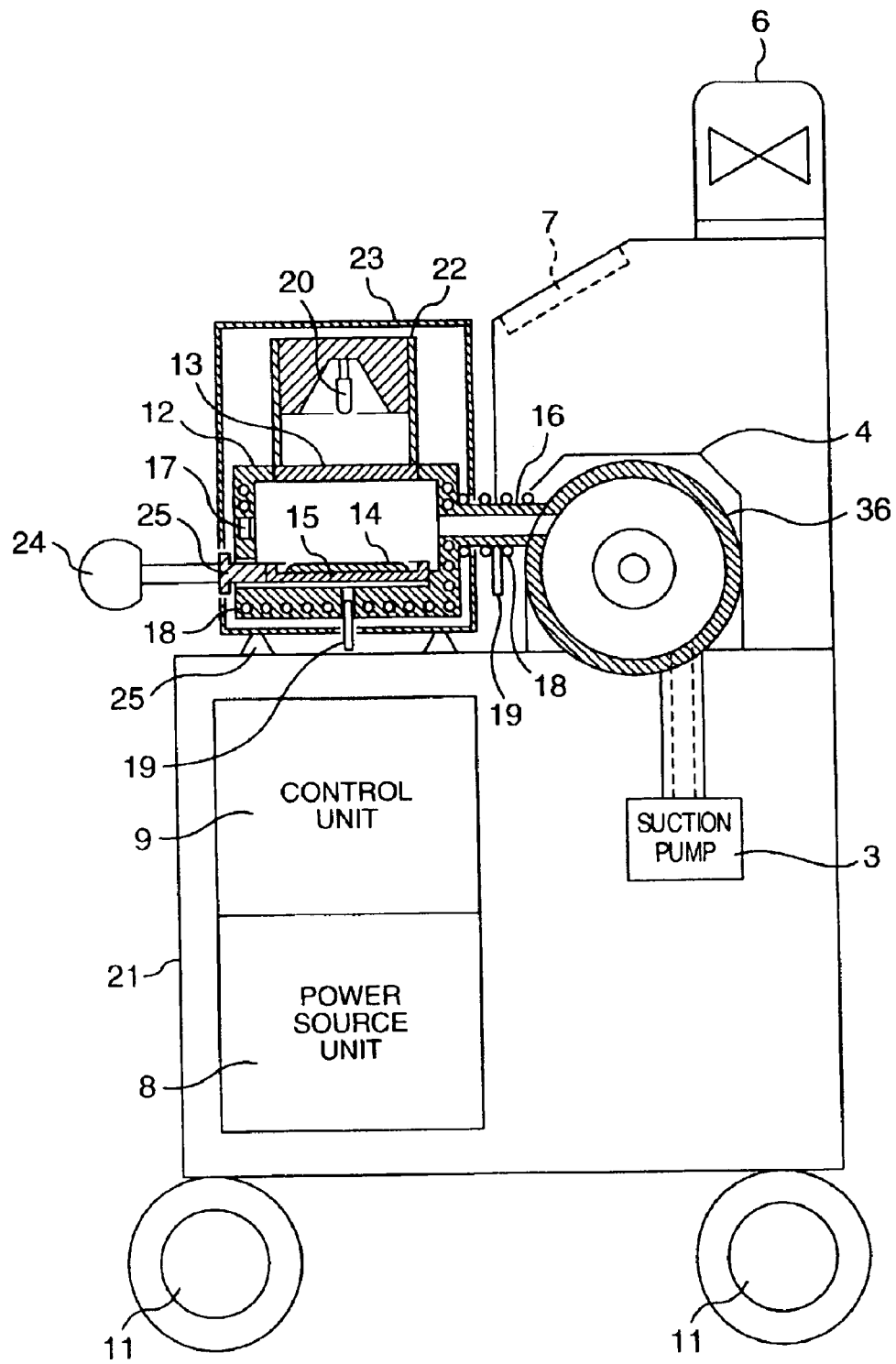
FIG. 3 is a partially sectioned side view illustrating the configuration of the dangerous substance detecting apparatus according to the first embodiment of the present invention.

FIG. 3 is a partially sectioned side view illustrating the configuration of the portable dangerous substance detecting apparatus according to the first embodiment of the present invention. When the x-, y- and z-axes are defined as shown in FIG. 2, a chamber 12 has a plane of symmetry parallel with a yz-plane. In FIG. 3, the cross section is taken on the plane of symmetry of the chamber 12, while the side view is taken from the positive direction of the x-axis.

Figure 4:
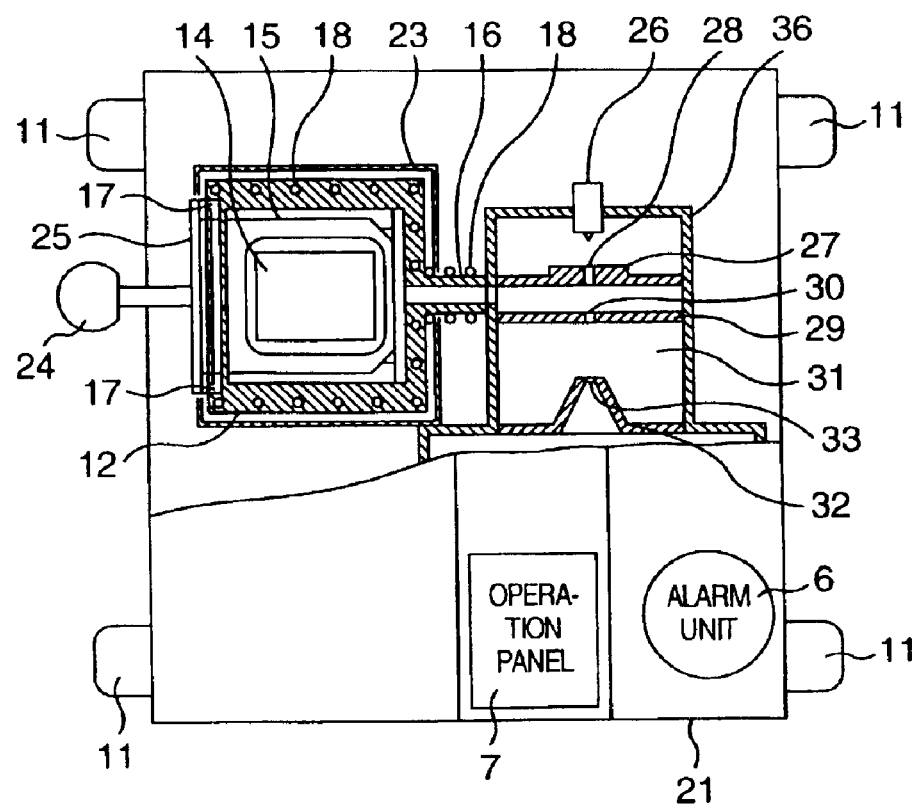
FIG. 4 is a partially sectioned top plan view illustrating the configuration of the dangerous substance detecting apparatus according to the first embodiment of the present invention.

FIG. 4 is a partially sectioned top plan view illustrating the configuration of the portable dangerous substance detecting apparatus according to the first embodiment of the present invention. In FIG. 4, the cross section is taken on a plane which is parallel with the plane (xy-plane) perpendicular to the plane of symmetry of the chamber 12, and passes through the center of an inlet pipe 16, while the top plan view is taken from the positive direction of the z-axis.

The oven 1 comprises the box type chamber 12 having a glass window 13, and a light source disposed at a position opposing the glass window 13 for emitting infrared rays. The oven 1 is covered with the cover 23 for heat insulation and light shielding. Here, a 150-Watt halogen lamp 20 is used for the light source for emitting infrared rays. The halogen lamp 20 basically comprises a tube made of quartz glass, a tungsten filament, and a reflective mirror. The tungsten filament is enclosed in the quartz glass which is filled with a halogen gas. As a current is applied, the tungsten filament incandesces to radiate light. The radiated light is reflected by the reflective mirror in one direction. The reflected light comprises infrared rays which have a maximum energy distribution mainly in a wavelength band from 0.7 $\mu$m to 2 $\mu$m. The halogen lamp 20 is supported on the housing 21 of the apparatus by a supporting member 22. A glass made of Kovar is used for the glass window 13 because it excels in the transmissivity for the wavelengths in the infrared region.

A test slip 14, which has been used to wipe the surface of an object under testing, is placed on the sample base 15, and carried into the sample base 15 from an insert port of the chamber 12. A handle 24 of the sample base 15 contacted by the operator is insulated from the chamber 12 by an insulating material 25 to maintain the contact sensible temperature substantially at a room temperature, so that the safety is assumed for the operator during the operation. The chamber 12 is connected to the ion source unit 2 through the inlet pipe 16. The chamber 12 is provided with a suction hole 17 such that the chamber 12 is sucked by a suction pump 3.

A heat source 18 and a thermometer 19 are disposed in the chamber 12 and the inlet pipe 16 for heating these components to prevent a sample and/or contaminants from adsorbing on the inner wall of the chamber 12 or to promote desorption of the sample and/or contaminants adsorbed on the inner wall of the chamber 12. Here, resistive heating is used for the heat source 18. The power supplied to the heat source 18 is controlled by the control unit 9 based on an output signal of the thermometer 19 so that the chamber 12 and inlet pipe 16 can be heated to and maintained at a desired temperature in a range of the room temperature to 300° C.

Operating conditions for the oven 1 are entered from the operation panel 7 as part of operating conditions specified for the respective components of the apparatus, so that the respective components of the apparatus, including the oven 1, are controlled by the control unit 9 based on the operating conditions entered from the operation panel 7.

The following description will be centered on a procedure for testing an object under testing for dangerous substances using the dangerous substance detecting apparatus according to the first embodiment.

Generally, in course of handling or transporting dangerous substances such as explosives, medication and the like, infinitesimal dangerous substances are highly likely to stick to the body of a human who handles the dangerous substances or on personal effects such as clothing, bag and the like. Therefore, a clean test slip (wiping member) for sampling is used to wipe the body of a human under testing or on the surface of an object under testing to provide particles wiped by the test slip as a test sample. The test slip is heated to evaporate the sample from the surface of the test slip on which the particles are stuck. Then, the evaporated sample is ionized to perform a mass analysis on the ions to determine the presence or absence of dangerous substances.

After the operator has wiped particles stuck on the surface of an object under testing such as a bag using the test slip 14 to collect a sample, the operator draws the sample base 15 out of the chamber 12, orients upward the surface of the test slip 14 on which the sample is stuck, places the test slip 14 thus oriented on the sample base 15, and pushes the sample base 15 into the chamber 12. The temperature in the chamber 12 is desirably set at 100° C. or higher.

After inserting the sample base 15 into the chamber 12, the halogen lamp 20 is powered for several seconds for emitting light. Here, the amount of supplied power is approximately 70 Watts, and the irradiation time is six seconds, in which case the test slip 14 reaches approximately 190° C. by actual measurement. Upon start of light emission from the halogen lamp 20, the surface of the test slip 14, on which the sample (particles) is stuck, is rapidly heated to promote rapid evaporation of the sample stuck on the test slip 14.

The evaporated sample is carried into a space between a first porous electrode 29 and an opposite electrode 27 in the ion source unit 2 through the inlet pipe 16 by the suction pump 3. A needle electrode 26 is disposed in the ion source unit 2 to apply a high voltage between the needle electrode 26 and opposite electrode 27. Corona discharge is generated near the leading end of the needle electrode 26 to first ionize nitrogen, oxygen, steam and the like. These ions are called the "primary ions." The primary ions are moved toward the opposite electrode 27 by an electric field. The evaporated sample carried into the space between the first porous electrode 29 and opposite electrode 27 flows into a space, in which the needle electrode 26 is disposed, through an opening 28 formed through the opposite electrode 27, and reacts with the primary ions and ionized. This method of generating the primary ions using the corona discharge in the atmosphere and utilizing the chemical reaction of the primary ions with the evaporated sample to ionize chemical substances within the sample is called an "atmospheric chemical ionization method."

The ion source unit 2 is provided with a heat source (not shown) and a thermometer (not shown). The power supplied to the heat source is controlled by the control unit 9 based on an output signal from the thermometer. The ion source unit 2 is heated to and maintained at a desired temperature at all times such that the evaporated sample does not adsorb on the interior of the ion source unit 2.

There is a potential difference of approximately 1 kV between the opposite electrode 27 and first porous electrode 29, so that ions are attracted toward the first porous electrode 29 and trapped into a differential exhaust system 31 through a first ion introduction pore 30. In the differential exhaust system 31, adiabatic expansion occurs to give rise to so-called clustering in which solvent molecules and the like stick to the ions. For reducing the clustering, the first porous electrode 29 and second porous electrode 32 are desirably heated by a heater or the like.

The ions of the sample generated by the atmospheric chemical ionization method are introduced into the mass analysis unit 4 through the first ion introduction pore 30 of the first porous electrode 29, differential exhaust system 31 exhausted by an exhaust system 10, and a second ion introduction pore 33 of the second porous electrode 32. The mass analysis unit 4 is exhausted by the exhaust system 10. The ion source unit 2 and mass analysis unit 4 make up a single container 36.

The ions of the sample introduced into the mass analysis unit 4 undergo a mass analysis by a quadrupole mass spectrometer. The apparatus has been previously set the values of m/e required for identifying a single or a plurality of dangerous substances to be detected. Output signals of a detector associated with the mass spectrometer, related to the values m/e required for identifying respective dangerous substances to be detected, are continuously sent to the data processing unit 5 at predetermined time intervals as the result of the mass analysis on the ions of the sample for data processing. The data processing unit 5 has a storage means which stores in the form of a database mass analysis data (the values m/e and relative strengths) required for identifying a plurality of dangerous substances such as explosives, medication and the like, and determination thresholds for the signal strength which are relied on to determine the identification of dangerous substances. The value m/e included in the signal sent to the data processing unit 5 is compared with the database read from the storage means. When the value m/e is identified as a stored value m/e associated with a certain dangerous substance, and the strength of the sent signal is larger than the determination threshold, the operator is notified of possible existence of the dangerous substance by the alarm unit 6 or the like.

Since a larger amount of evaporated sample sent to the ion source unit 2 causes a higher ion concentration of a dangerous substance generated by the ion source unit 2, a signal having a larger strength is generated by the mass analysis unit 4. Consequently, with the resulting signal strength higher than the determination threshold set in the data processing unit 5, the determination can be readily made on the identification of a dangerous substance to make a secure testing for the presence or absence of the dangerous substance.

Figure 5:
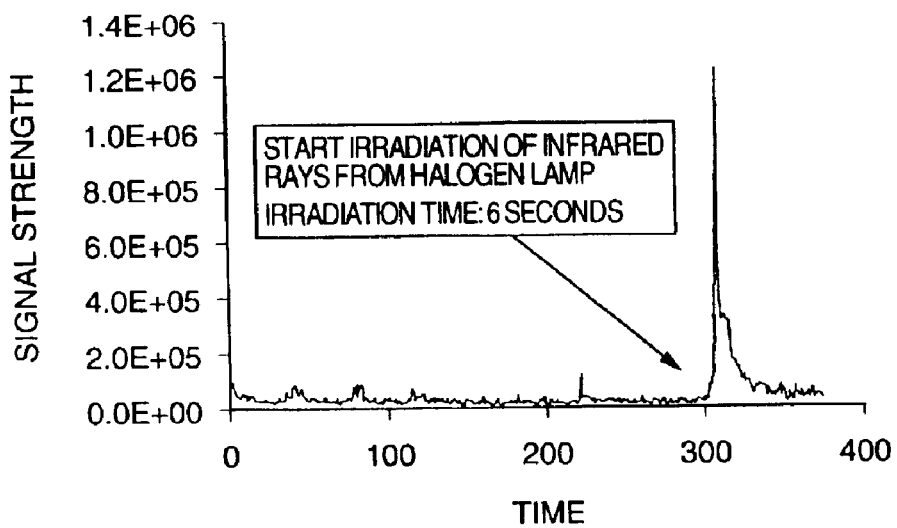
FIG. 5 is a graph showing a change over time in the strength of a signal indicative of trinitrotoluene having m/e=227, measured by irradiating an object under testing with infrared rays from a halogen lamp in the dangerous substance detecting apparatus according to the first embodiment of the present invention.

FIG. 5 is a graph showing a change over time in the strength of a signal indicative of trinitrotoluene (TNT) having m/e=227, is measured by irradiating a sample with infrared rays from the halogen lamp for six seconds in the dangerous substance detecting apparatus according to the first embodiment of the present invention.

Figure 6:
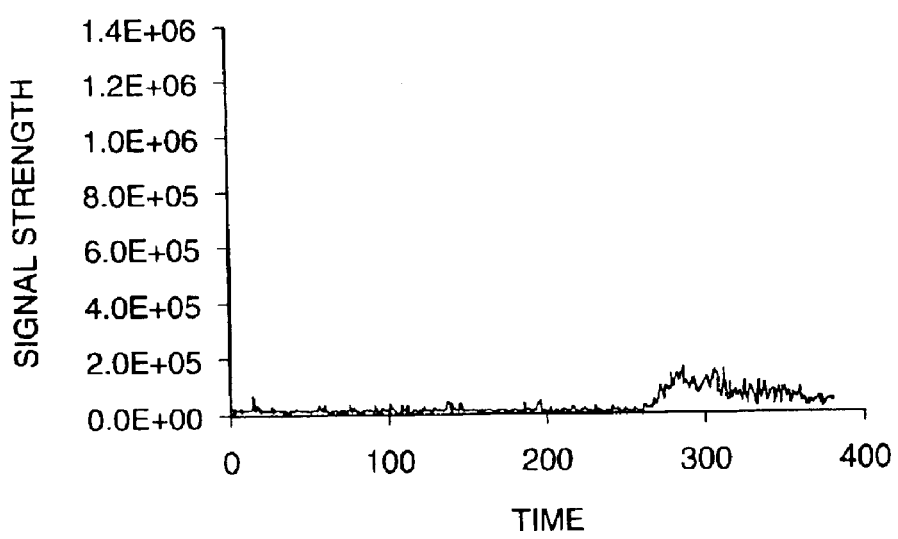
FIG. 6 is a graph showing a change over time in the strength of the signal indicative of trinitrotoluene having m/e=227, measured without irradiation of infrared rays in the dangerous substance detecting apparatus according to the first embodiment of the present invention.
Figure 15:
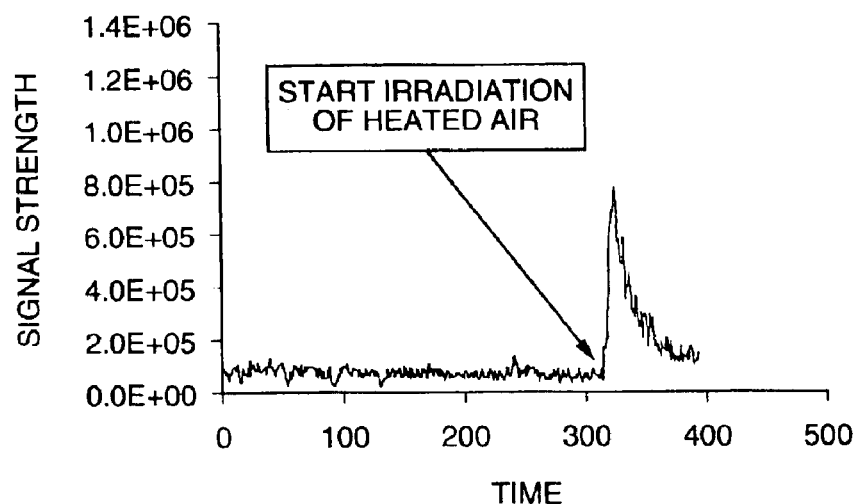
FIG. 15 is a graph showing a change over time in the strength of a signal indicative of trinitrotoluene having m/e=227, measured by irradiating an object under testing with heated air in the dangerous substance detecting apparatus according to the fourth embodiment of the present invention.

FIG. 6 is a graph showing a change over time in the strength of a signal indicative of trinitrotoluene (TNT) having m/e=227, measured without irradiation of infrared rays from the halogen lamp in the dangerous substance detecting apparatus according to the first embodiment of the present invention. In FIGS. 5, 6 and 15, E represents exponential, and the horizontal axis represents the time in seconds.

FIG. 5 clearly shows a sharp signal waveform with m/e=227 indicative of the existence of trinitrotoluene, the strength of which suddenly increases substantially simultaneously with the start of irradiation of the infrared rays from the halogen lamp 20 and suddenly falls in synchronism with the finish of the irradiation of the halogen lamp 20. When the halogen lamp 20 is not irradiated, a broad waveform with m/e=227 indicative of the existence of trinitrotoluene, as shown in FIG. 6, has a slowly increasing strength. As appreciated from a comparison of the results of the experiments in FIGS. 5 and 6, the signal waveform indicative of the existence of trinitrotoluene has a strength seven times or more higher when the infrared rays are irradiated than when no infrared rays are irradiated. The irradiation of the infrared rays ensures that a dangerous substance can be detected with less probability of erroneous report.

If the test slip 14 is left in the chamber 12 due to a failure of the operator, impurities can be evaporated from the test slip 14 to possibly cause contamination of the oven 1 and/or ion source unit 2, burnt test slip 14, and the like. For purposes of obviating such a situation, an alarm may be generated when a certain time elapses after the insertion of the test slip 14 into the chamber 12 in order for the operator not to forget to remove the test slip 14 after the end of the test. As a sensor (not shown) senses the test slip 14 inserted into the chamber 12, a timer, implemented by a program in the control unit 9, is started. If a time set by the program is exceeded by the time from the insertion of the test slip 14 into the chamber 12 to the removal of the test slip 14 from the chamber 12 after the end of the test, an alarm is generated on the operation panel 7 for warning that the operator forgets to remove the test slip 14. In this way, it is possible to prevent the contamination in the ion source unit 2, burnt test slip 14, and the like due to the operator who forgets to remove the test slip 14 from the chamber 12.

Assuming that impurities or residual dangerous substances adsorb on the carrier surface of the sample base 15 and/or the inner wall of the chamber 12, they may be evaporated when the test slip 14 is irradiated with infrared rays, ionized, and carried into the mass analysis unit 4 to erroneously detect the dangerous substances which do not actually exist on the test slip 14. Therefore, the oven 1 must be cleaned on a periodic basis for preventing such an erroneous detection. The carrier surface of the sample base 15 and the inner wall of the chamber 12 can be irradiated with infrared rays generated from the halogen lamp 20 to heat the irradiated regions to high temperatures in an extremely short time. In this way, the impurities or residual dangerous substances adsorbed on the carrier surface of the sample base 15 and/or the inner wall of the chamber 12, possibly causing an erroneous report, can be desorbed in an extremely short time. The residual dangerous substances thus desorbed are exhausted from the oven 1. In this way, the interior of the oven 1 can be effectively cleaned in a short time without burdening the operator with the cleaning, to advantageously provide an additional improvement on the reliability and working rate of the apparatus.

It is essential to minimize the total power consumption of the dangerous substance detecting apparatus according to the present invention which additionally comprises the power-consuming halogen lamp 20.

Figure 7:
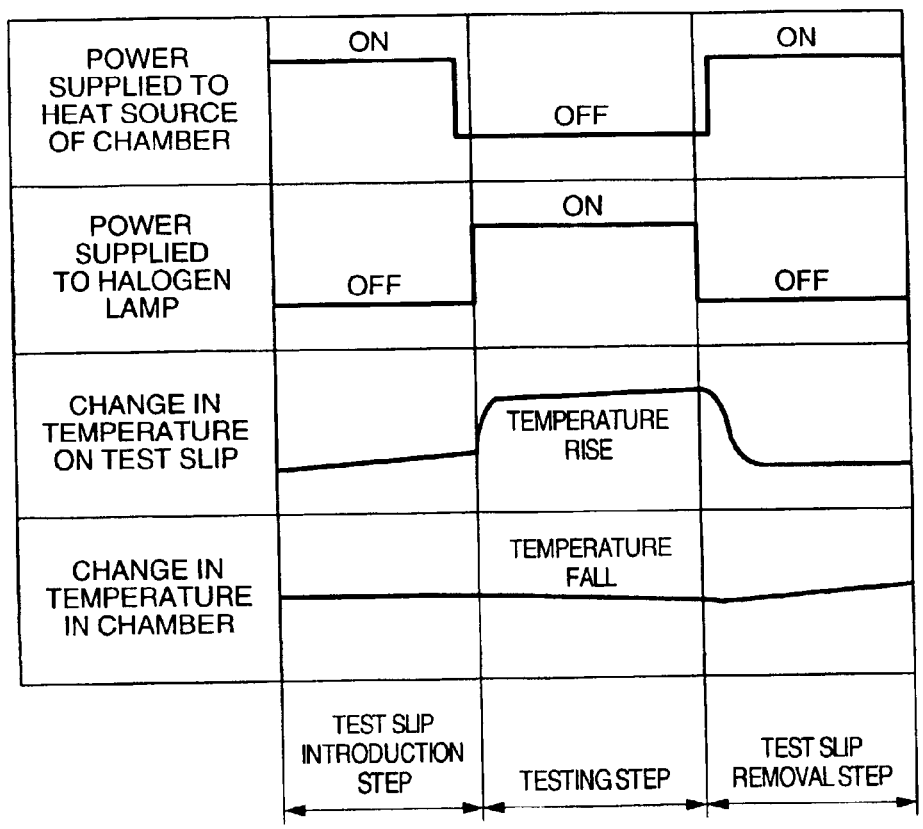
FIG. 7 is a graph used for explaining an exemplary relationship between supplied power for heating and changes in temperature in respective steps of a dangerous substance detection performed by the dangerous substance detecting apparatus according to the first embodiment of the present invention.

FIG. 7 is a graph used for explaining an exemplary relationship between the supplied power for heating and changes in temperature in respective steps of the dangerous substance detection performed by the dangerous substance detecting apparatus according to the first embodiment of the present invention. FIG. 7 shows a manner of controlling the power supplied to the halogen lamp 20 and to the heat source 18 of the chamber 12. As shown in FIG. 7, the power supply control features that the power is not simultaneously supplied to the halogen lamp 20 and the heat source 18 of the chamber 12. In other words, the power is alternately supplied to the halogen lamp 20 and to the heat source 18 of the chamber 12.

In a test slip introduction step for introducing the test slip 14 into the chamber 12, the heat source 18 of the chamber 12 is powered ON, while the halogen lamp 20 is powered OFF.

In a testing step which involves heating the test slip 14 introduced into the chamber 12 to evaporate dangerous substances stuck on the test slip 14, ionizing the evaporated dangerous substances for a mass analysis, and determining the presence of the dangerous substances based on an output signal from the detector in the mass analysis unit 4 to identify the kinds of the detected dangerous substances, the heat source 18 of the chamber 12 is powered OFF, while the halogen lamp 20 is powered ON. The test slip 14 is heated in an extremely short time with the irradiation of infrared rays from the halogen lamp 20.

For preventing temporary consumption of large power upon transfer from the test slip introduction step to the testing step, the heat source 18 of the chamber 12 is powered OFF before the halogen lamp 20 is powered ON.

In a test slip removal step for removing the test slip 14 from the chamber 12, the heat source 18 of the chamber 12 is powered ON, while the halogen lamp 20 is powered OFF, as is the case with the test slip introduction step.

As shown in FIG. 5, a sample derived from dangerous substances can be evaporated and ionized in a high concentration by irradiating the test slip 14 with infrared rays from the halogen lamp 20 for several seconds. Therefore, even if the heat source 18 of the chamber 12 is powered OFF for an extremely short time in which the test slip 14 is irradiated with infrared rays from the halogen lamp 20, the thermal capacity of the chamber 12 prevents the same from a sudden drop in temperature which would induce adsorption of impurities, dangerous substances and the like on the inner wall of the chamber 12. When the halogen lamp 20 is driven to irradiate the test slip 14 with infrared rays for six seconds, the chamber 12 is cooled down by approximately 2° C. on average for the six seconds.

By controlling the power supply as shown in FIG. 7, the dangerous substance detection can be carried out without increasing the total power consumption. The portable dangerous substance detecting apparatus according to the first embodiment can be basically transported to an arbitrary region in or out of Japan and operated in the destination to conduct a test for detecting dangerous substances. Specifically, the dangerous substance detecting apparatus can be operated within the range of the domestic power of 100 volts, 15 amperes, which is generally provided in Japan. Consequently, the dangerous substance detecting apparatus can improve the mobility because it does not depend on the location and does not require a separate power supply or a device associated with the power supply.

Figure 8:
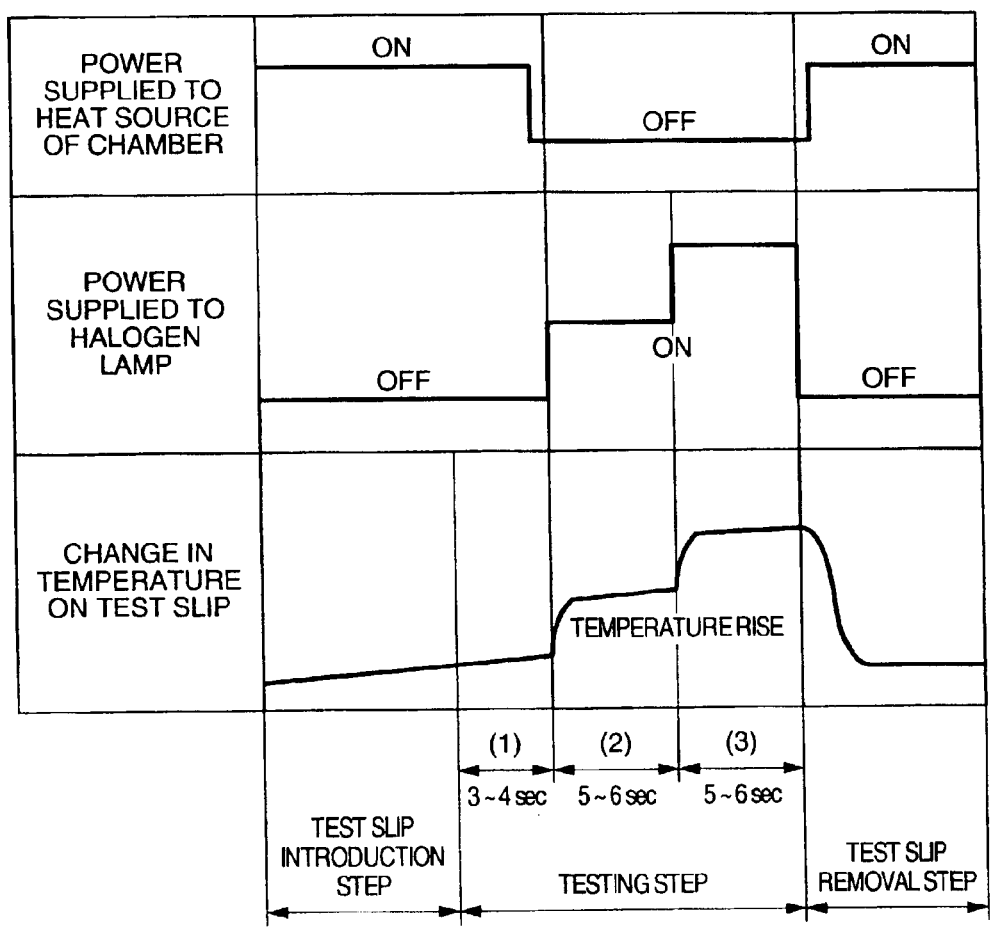
FIG. 8 is a graph used for explaining another exemplary relationship between the supplied power for heating and a change in temperature in the respective steps of the dangerous substance detection performed by the dangerous substance detecting apparatus according to the first embodiment of the present invention.

FIG. 8 is a graph used for explaining another exemplary relationship between the supplied power for heating and a change in temperature in the respective steps of the dangerous substance detection performed by the dangerous substance detecting apparatus according to the first embodiment of the present invention. FIG. 8 shows another manner of controlling the power supplied to the halogen lamp 20 and to the heat source 18 of the chamber 12. As is the case with FIG. 7, the power is not simultaneously supplied to the halogen lamp 20 and the heat source 18 of the chamber 12 in FIG. 8. The control shown in FIG. 8 differs in that the halogen lamp 20 is powered in steps. The following description will be centered on differences between the power supply controls shown in FIGS. 7 and 8.

The power supply control shown in FIG. 8 features that the power supplied to the halogen lamp 20 is sequentially increased in steps in the testing step, and that the testing step is started before the halogen lamp 20 is powered ON. Since the halogen lamp 20 is powered in steps, the test slip 14 can also be heated in steps.

Generally, different kinds of substances evaporate at different temperatures at the atmospheric pressure. Therefore, as the test slip 14 is sequentially heated in steps, different dangerous substances are evaporated from the test slip 14 depending on the temperature of the test slip 14, so that the dangerous substance detecting apparatus can identify in the testing step different dangerous substances which are sensed at respective temperatures to which the test slip 14 is heated. In addition, even with a sample under testing which includes a plurality of dangerous substances, the power supply control shown in FIG. 8 permits the dangerous substance detecting apparatus to sequentially detect and identify different kinds of dangerous substances. Furthermore, since the test slip 14 can be sequentially heated to desired temperatures, the chamber 12 can be held at low temperatures at which no impurities adsorb on the inner wall of the chamber 12. Thus, the resulting dangerous substance detecting apparatus can efficiently detect a variety of dangerous substances which evaporate at different temperatures without fail.

For example, in the embodiment shown in FIG. 8, a first test is conducted without powering the halogen lamp 20 in a testing step (1). In the testing step (1), the test slip 14 is slowly heated by a convective heat transfer and a contact heat transfer from the inner wall of the chamber 12. In the testing step (1), the dangerous substance detecting apparatus tests the test slip 14 for the presence or absence of a dangerous substance which exhibits a low evaporation temperature, for example, nitroglycerin or the like. The testing step (1) takes a time, for example, in a range of three to four seconds. In a testing step (2), the halogen lamp 20 is powered to heat the surface of the test slip 14, which has been used to wipe an object under testing, to approximately 150° C. In the testing step (2), the dangerous substance detecting apparatus tests the test slip 14 for the presence or absence of a dangerous substance which exhibits a high evaporation temperature, for example, trinitrotoluene (TNT). In a testing step (3), the power to the halogen lamp 20 is further increased to heat the wiping surface of the test slip 14 to approximately 200° C. In the testing step (3), the dangerous substance detecting apparatus tests the test slip 14 for the presence or absence of a dangerous substance which exhibits the highest evaporation temperature, for example, trimethylenetrinitroamine (RDX). The testing steps (2), (3) take a time, for example, in a range of five to six seconds.

While in the exemplary power supply control shown in FIG. 8, the test slip 14 is heated to different temperatures in two steps, the test slip 14 may be heated in a plurality of steps more than two to detect a plurality of kinds of dangerous substances stuck on the test slip 14.

By conducting the power supply control shown in FIG. 8 to divide the testing step, the dangerous substance detecting apparatus can process an increased number of signals with different m/e values in the testing step. Since the testing step is divided into three in the embodiment of FIG. 8, the dangerous substance detecting apparatus can process the number of signals with different m/e values three times as much as the number of dangerous substances which can be tested in a single testing step shown in FIG. 7. In addition, the test slip 14 can be tested for more kinds of dangerous substances because the data processing unit 5 can identify more dangerous substances from a combination of detected signals with different m/e values in the respective testing steps at the end of the testing step (3).

By conducting the power supply control shown in FIG. 8 to divide the testing step, it is possible to reduce a time taken by the data processing unit 5 for the identity determination in each testing step. The number of signals with different m/e values which can be identified by the data processing unit 5 in a fixed time depends on the performance of the data processing unit 5. For testing the test slip 14 for whatever dangerous substances stuck thereon in a single testing step, the data processing unit 5 needs a processing time in accordance with the number of signals with different m/e values under processing, or must limit kinds of dangerous substances under testing. In the exemplary power supply control shown in FIG. 8, the testing step is divided into the number of different temperatures to which the surface of the test slip 14 is heated. The data processing unit 5 may previously acquire data on signals with different m/e values indicative of different dangerous substances which efficiently evaporate from the surface of the test slip 14 at a particular temperature set to each testing step to limit the number of signals with different m/e values which are to be tested. Consequently, the data processing unit 5 processes a less number of signals in each testing step, resulting in a reduction in the processing time required for the identity determination.

In the power supply controls shown in FIGS. 7 and 8, the halogen lamp 20 may be supplied with low standby power of several Watts, instead of completely shutting off the power to the halogen lamp 20, without causing any problem.

(Second Embodiment)

Figure 9:
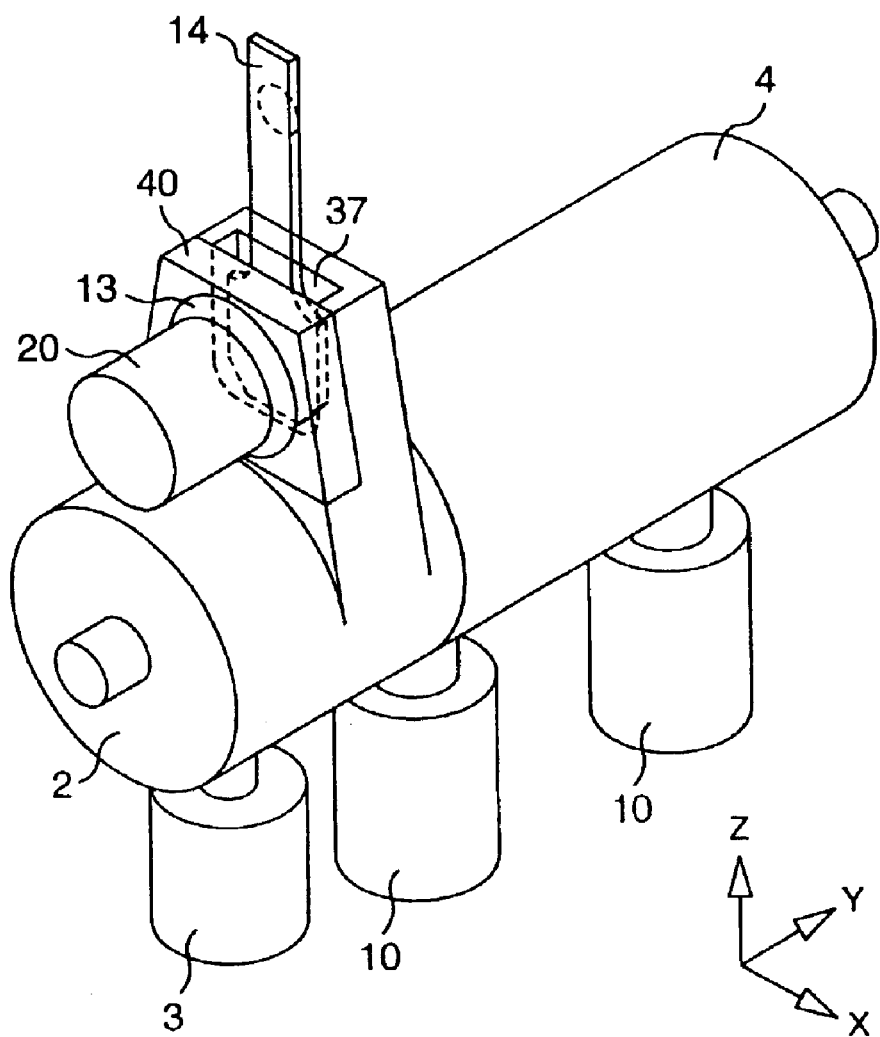
FIG. 9 is a perspective view illustrating the appearance of the main configuration in a dangerous substance detecting apparatus according to a second embodiment of the present invention.

FIG. 9 is a perspective view illustrating the main configuration of a portable dangerous substance detecting apparatus according to a second embodiment of the present invention, showing a wiping member inserted into a test slip receiver. In FIG. 9, components illustrated in FIG. 1 are omitted except for the ion source unit 2, mass analysis unit 4, exhaust system 10, suction pump 3, halogen lamp 20, and test slip receiver 37. A relative positioning of the test slip receiver 37 to the ion source unit 2 can be changed as appropriate depending on the direction in which the test slip 14 is inserted into the test slip receiver 37.

Figure 10:
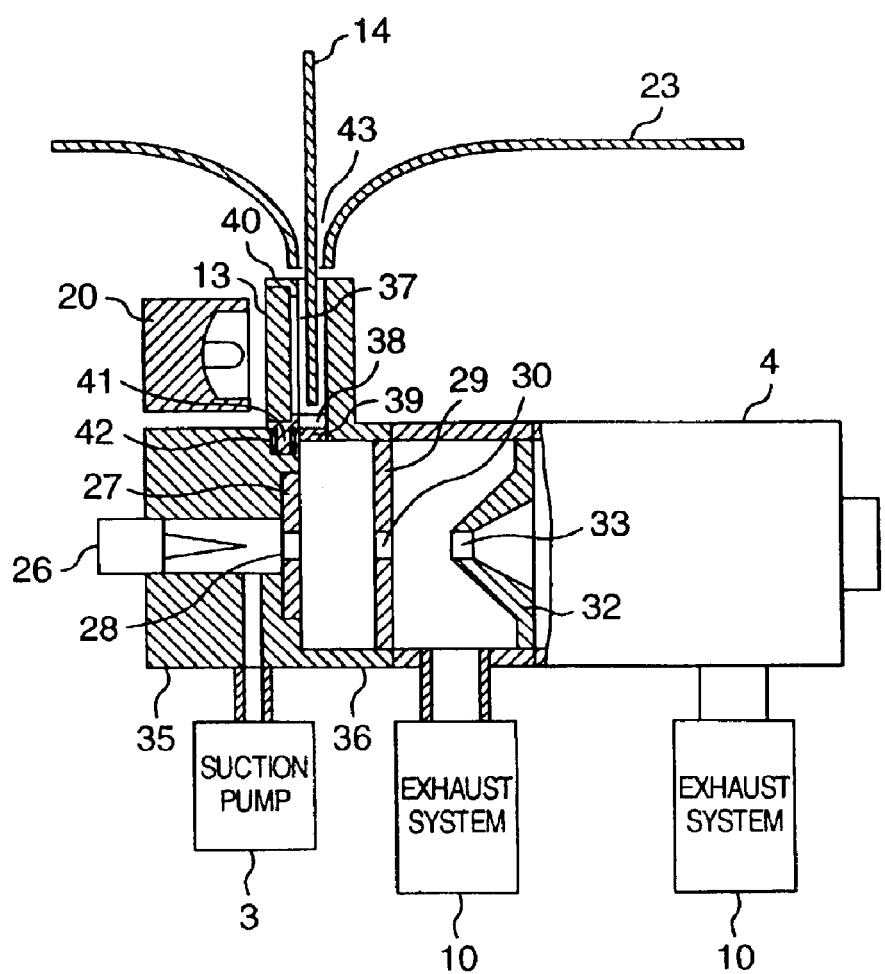
FIG. 10 is diagram illustrating the main configuration of the dangerous substance detecting apparatus according to the second embodiment of the present invention, including a cross-section of a test slip receiver loaded with a wiping member (test slip), and a partially sectioned view of an ion source unit.

FIG. 10 is a diagram illustrating the main configuration of the portable dangerous substance detecting apparatus according to the second embodiment of the present invention, showing a side view including a cross section of the test slip receiver loaded with the wiping member, and a partially sectioned view of the ion source unit.

When the x-, y- and z-axes are defined as shown in FIG. 9, the test slip receiver 37 has a plane of symmetry parallel with the yz-plane. In FIG. 10, the cross section is taken on the plane of symmetry of the test slip receiver 37, while the side view is taken from the positive direction of the x-axis.

Figure 11:
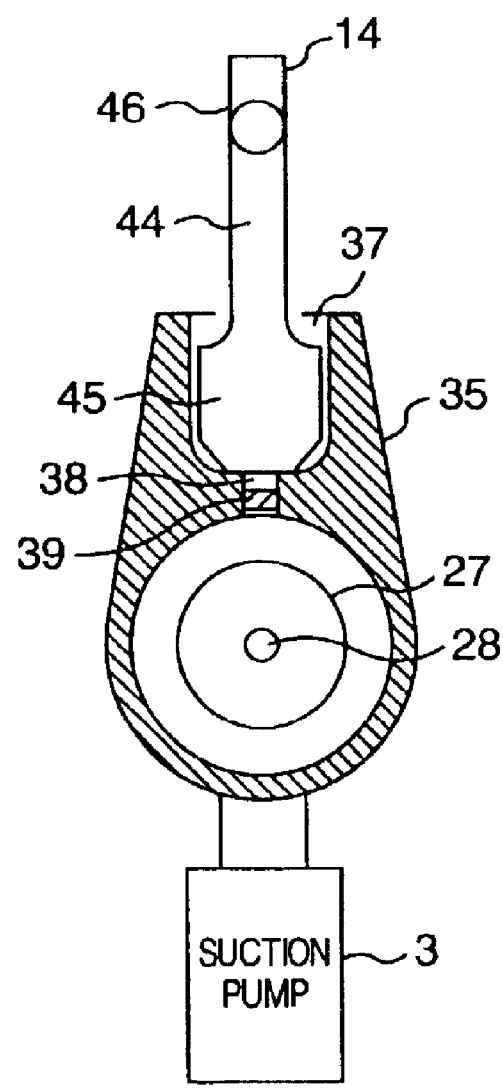
FIG. 11 is a partially sectioned view illustrating the shape of a flat wiping member which is inserted into the test slip receiver in the dangerous substance detecting apparatus according to the second embodiment of the present invention.

FIG. 11 is a partially sectioned front view of the dangerous substance detecting apparatus according to the second embodiment of the present invention, showing the shape of a flat wiping member which is inserted into the test slip receiver. In FIG. 11, the cross section is taken on a plane which is in parallel with the plane (xz-plane) perpendicular to the plane of symmetry of the test slip receiver and passes through the center of an introduction hole 38, while the front view is taken from the positive direction of the y-axis.

The apparatus according to the second embodiment features that the oven 1 is integrated with the ion source unit 2 in the apparatus according to the first embodiment.

Except for the integration of the oven 1 with the ion source unit 2, and the use of the same heat source, not shown in FIG. 10, for heating the ion source unit 2 and the test slip receiver 37 loaded with the test slip 14 which serves as the wiping member that holds a wiped object under testing, the second embodiment is the same as the first embodiment in the remaining configuration, the power supply control for heating in the respective steps of the dangerous substance detection, and the determination on the identity of dangerous substances, so that description on such aspects is omitted.

In the ion source unit 2 of the dangerous substance detecting apparatus according to the second embodiment, the needle electrode 26, opposite electrode 27, and porous electrode 29 are held in a flange 35. The test slip receiver 37 is disposed above the flange 35 for inserting the test slip 14 thereinto. The test slip receiver 37 is formed with the introduction hole 38, on the bottom, which extends to a space between the opposite electrode 27 and porous electrode 29. A filter 39 is inserted into the introduction hole 38 for preventing foreign substances from introducing into the ion source unit 2. In addition, the test slip receiver 37 is formed with a movable wall 40, on one side, which can be readily removed.

A pin 41 is embedded in a lower end of the movable wall 40, while the flange 35 is formed with a hole at a position corresponding to the pin 41 for inserting a resilient body 42 in a shape which has a spring property in a circumferential direction. The resilient body 42 has an inscribed circle diameter smaller than the outer diameter of the pin 41. As the pin 41 of the movable wall 40 is pushed into the annular resilient body 42, the resilient body 42 is deformed to hold the pin 41, thereby holding the movable wall 40 coupled to the flange 35. A glass window 13 made of Kovar is fixed in the movable wall 40, and the halogen lamp 20 is securely disposed at a position opposing the glass window 13.

While the ion source unit 2 and the like are covered by the cover 23 of the housing 21 of the apparatus, the test slip receiver 37 is provided with an insertion port 43 on the top face, which is sloped to facilitate the insertion of the test slip 14 that serves as the wiping member.

The test slip 14, which is the wiping member that has been used to wipe an object under testing, is inserted into the test slip receiver 37 through the insertion port 43. Since the insertion port 43 is sloped, the test slip 14 can be smoothly inserted into the test slip receiver 37 without catch or jam.

The test slip 14, which is the wiping member used in the second embodiment, is in the shape of a ladle, as illustrated in FIGS. 10 and 11, which has a thickness, for example, in a range of 1 mm to 5 mm. The test slip 14 is clearly divided into a grip section (handle section) 44 grabbed by the operator and a testing section (wiping section) 45 with which the object under testing has been wiped.

When the test slip 14 remains inserted into the test slip receiver 37, the grip section 44 protrudes from the cover 23 of the housing 21 of the apparatus. The grip section 44 has a circle mark 46 (means for identifying the surface on which the sample is stuck) on the side held by a hand. The mark 46 is printed on a surface opposite to the testing section 45 (wiping surface). This mark 46 permits the operator to wipe the object under testing with the wiping member 14, without wiping with the opposite surface by mistake, and readily insert the wiping member 14 into the insertion port 43. Even if the operator makes a mistake in the insertion, the wiping member 14 protrudes from the cover 23 of the housing 21 of the apparatus, so that the operator can readily view the mistake. Of course, the mark 46 may be applied on the testing section 45 with which the object under testing is wiped, or the mark 46 may be applied on the surface on the same side as the testing section 45 (wiping surface).

A sensor (not shown) is disposed between the insertion port 43 and test slip receiver 37 for sensing the insertion of the test slip 14. As the sensor senses the insertion of the test slip 14, the halogen lamp 20 is powered with a delay to test the test slip 14 for dangerous substances, in a manner similar to the power supply control for the halogen lamp 20 and the heat source 18 of the chamber 12, as shown in FIGS. 7 and 8.

In addition, for preventing the operator from forgetting to remove the test slip 14 from the test slip receiver 37 after the end of the test, an alarm is generated when a certain time elapses after the sensor (not shown) has sensed the insertion of the test slip 14 into the insertion section 37.

In the configuration of the second embodiment, since the oven 1 and introduction pipe 16, required in the first embodiment, are eliminated, the following advantages are provided.

A first advantage lies in an improvement on the detection sensitivity. According to the configuration in the second embodiment, a sample (particles) stuck on the test slip 14 is evaporated, and the evaporated sample is directly sent into the space between the first porous electrode 29 and opposite electrode 27 in the ion source unit 2 by the suction pump 3. In this event, since the ion source unit 2 is heated, the evaporated sample will not adsorb onto the introduction hole 38. This results in a lower possibility of the lost sample due to the adsorption onto the chamber 12 and introduction port 16, as would be found in the first embodiment. Also, since the test slip receiver 37 can be made significantly smaller in volume than the chamber 12 in the first embodiment to largely reduce the dilution of the vapor caused by the volume of the space in which the sample is evaporated, the evaporated sample can be sent to the ion source unit 2 in a high concentration to generate ions in a higher concentration than in the first embodiment, thereby sensing without fail the existence of infinitesimal dangerous substances stuck on the test slip 14.

A second advantage lies in the elimination of the oven 1 and introduction pipe 16 in the first embodiment, resulting in a large reduction in the number of parts to provide an inexpensive and compact apparatus.

A third advantage lies in a procedure after the operator has wiped the object under testing, which is completed through simple operations comprised of the insertion of the test slip 14 into the test slip receiver 37 and the removal of the test slip 14 from the test slip receiver 37. Thus, the operator has less opportunities to touch heated components by mistake, and does not need special tools for handling the test slip 14. The resulting apparatus therefore provides high safety, operability and throughput.

A fourth advantage lies in ease of maintenance for the apparatus, resulting from the movable wall 40 which forms part of the test slip receiver 37. Though the test slip receiver 37 must be cleaned on a periodic basis, the movable wall 40 can be readily drawn off of the flange 35 in the configuration of the second embodiment to efficiently clean the inner wall of the test slip receiver 37 and replace the filter 39 in a short time.

(Third Embodiment)

Figure 12:
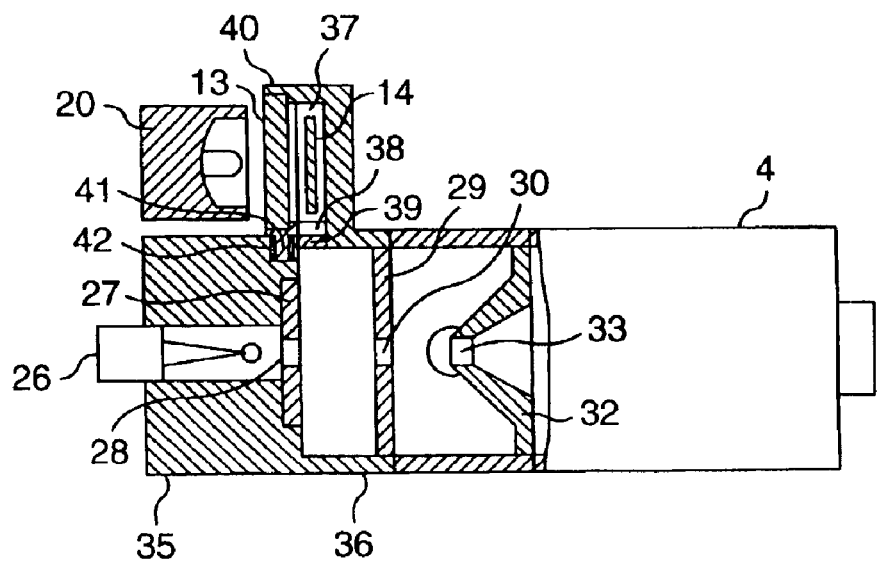
FIG. 12 is a diagram illustrating the main configuration of a dangerous substance detecting apparatus according to a third embodiment of the present invention, including a cross-section of a test slip receiver loaded with a wiping member, and a partially sectioned view of an ion source.

FIG. 12 is a top plan view illustrating the main configuration of a portable dangerous substance detecting apparatus according to a third embodiment of the present invention, including a cross section of a test slip receiver loaded with a wiping member, and a partially sectioned view of an ion source unit. In FIG. 12, the partially sectioned view is taken on a plane which includes the center of the needle electrode 26 of the ion source unit, is perpendicular to the opposite electrode 27, and is parallel with the xy-plane when the x-, y- and z-axes are defined as shown in FIG. 9. The top plan view in turn is taken from the positive direction of the z-axis.

Figure 13:
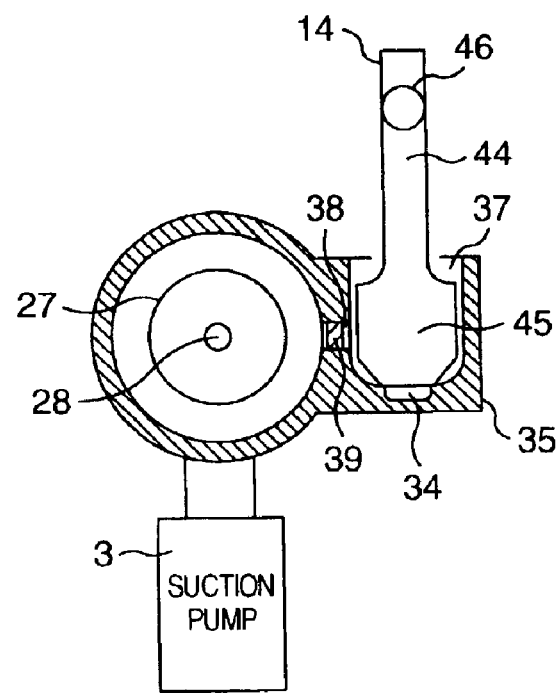
FIG. 13 is a partially sectioned view illustrating the shape of a flat wiping member which is inserted into the test slip receiver in the dangerous substance detecting apparatus according to the third embodiment of the present invention.

FIG. 13 is a partially sectioned front view illustrating a flat wiping member which is inserted into the test slip receiver in the dangerous substance detecting apparatus according to the third embodiment of the present invention. In FIG. 13, the partially sectioned view, which is a cross section including the center of the introduction hole 38 and in parallel with the opposite electrode 27, is taken on a plane parallel with the xz-plane, when the x-, y- and z-axes are defined as shown in FIG. 9. The front view is taken from the positive direction of the y-axis. The third embodiment is a modification to the second embodiment in the position of the test slip receiver 37. Specifically, the test slip receiver 37 is formed above the opposite electrode 27 in the second embodiment, while the test slip receiver 37 is formed alongside of the opposite electrode 27 in the third embodiment. Except for the test slip receiver 37 loaded with the test slip 14 which serves as the wiping member that holds a wiped object under testing, the introduction hole 38, and the filter 39 inserted into the introduction hole 38, the third embodiment is the same as the first and second embodiments in the remaining configuration, the power supply control for heating in the respective steps of the dangerous substance detection, and the determination on the identity of dangerous substances, so that description on such aspects is omitted.

In the third embodiment, the test slip receiver 37 is disposed alongside of the ion source unit 2, and the introduction hole 38 is formed through a side wall between the test slip receiver 37 and ion source unit 2 to be in communication with the space between the opposite electrode 27 and porous electrode 29. The filter 39 is inserted into the introduction hole 38 for preventing foreign substances from introducing into the ion source unit 2. A pool 34 is disposed on the bottom of the test slip receiver 37 for collecting debris. The pool 34 is recessed such that the test slip 14 inserted into the test slip receiver 37 does not come into direct contact with the pool 38 and such that the pool 38 is not directly irradiated with infrared rays from the halogen lamp 20. In the third embodiment, since the test slip receiver 37 associated with the test slip 14 is disposed alongside of the ion source unit 2, foreign substances such as debris, even if coming into the test slip receiver 37 together with the test slip 14, are less likely to directly introduce into the introduction hole 38, resulting in a reduction in clogging of the filter 39. Since the pool 34 is disposed on the bottom of the test slip receiver 37, foreign substances coming into the test slip receiver 37 can be collected at one spot to facilitate the cleaning. In addition, since the pool 34 is recessed, debris collected in the pool 34 will not come into contact with the next test slip 14 which would be inserted into the test slip receiver 37. It is therefore possible to prevent the debris from spreading over the test slip receiver 37, possibly caused by the debris sticking to the test slip 14 each time the test slip 14 is inserted into the test slip receiver 37. A consequent reduction in the clogging of the filter 39 can improve the working rate of the apparatus because the maintenance such as a replacement of the filter 39 and the like is required less frequently. The debris collected in the pool 34 is not directly heated by infrared rays from the halogen lamp 20 to be burnt, so that the safety is assured.

While the dangerous substance detecting apparatus according to the third embodiment comprises the pool 34 for collecting debris, the pool 34 may not be provided. In this case, a screen may be provided on the bottom of the test slip receiver 37 such that debris coming into the test slip receiver 37 together with the test slip 14 can be dropped beneath the test slip receiver 37 through the screen. In this way, the debris can be removed from the test slip receiver 37. Alternatively, without special countermeasures to debris, no problem arises in regard to the ease of maintenance, i.e., cleaning, because the test slip receiver 37 comprises the movable wall 40, which can be readily removed, on one side, as previously described in the second embodiment.

While the movable wall 40 is provided with the glass window 13 in the second and third embodiments, the halogen lamp 20 may be directly inserted into a hole formed through the movable wall 40, without forming the glass window 13. In this case, since the glass window 13 is eliminated, maintenance operations can be performed in safety when the halogen lamp 20 is replaced or when the movable wall 40 is attached or removed, because no glass window would be broken, and moreover, the apparatus can be manufactured at a lower cost.

While the test slip 14 is manually inserted into and removed from the test slip receiver 37 in the second and third embodiments, the dangerous substance detecting apparatus may be provided with an automatic carrier mechanism for automatically inserting and removing a plurality of test slips 14 into and from the test slip receiver 37 in sequence. In this case, since the operator can concentrate attention on the wiping operation, the throughput can be improved.

While the halogen lamp 20 is used in the second and third embodiments, it may not be used. Even if the halogen lamp 20 is not used, the integration of the oven 1 with the ion source unit 2 in the first embodiment provides similar advantages to those of the second embodiment, and can generate a higher strength of signal than the strength (see FIG. 6) of the signal indicative of trinitrotoluene having m/e=227, which is measured without irradiation of halogen lamp in the apparatus according to the first embodiment. In addition, since neither the halogen lamp 20 nor the glass window 13 is used, the apparatus can be manufactured at a lower cost.

In the configuration illustrated in the second and third embodiments, the test slip receiver 37 is open upward so that the test slip 14 is inserted into the test slip receiver 37 from above. Alternatively, the test slip receiver 37 may be open laterally so that the test slip 14 is inserted into the test slip receiver 37 sideways. In this configuration, the apparatus can be freely designed with respect to the relative positioning of the ion source unit 2 to the test slip receiver 37.

(Fourth Embodiment)

Figure 14:
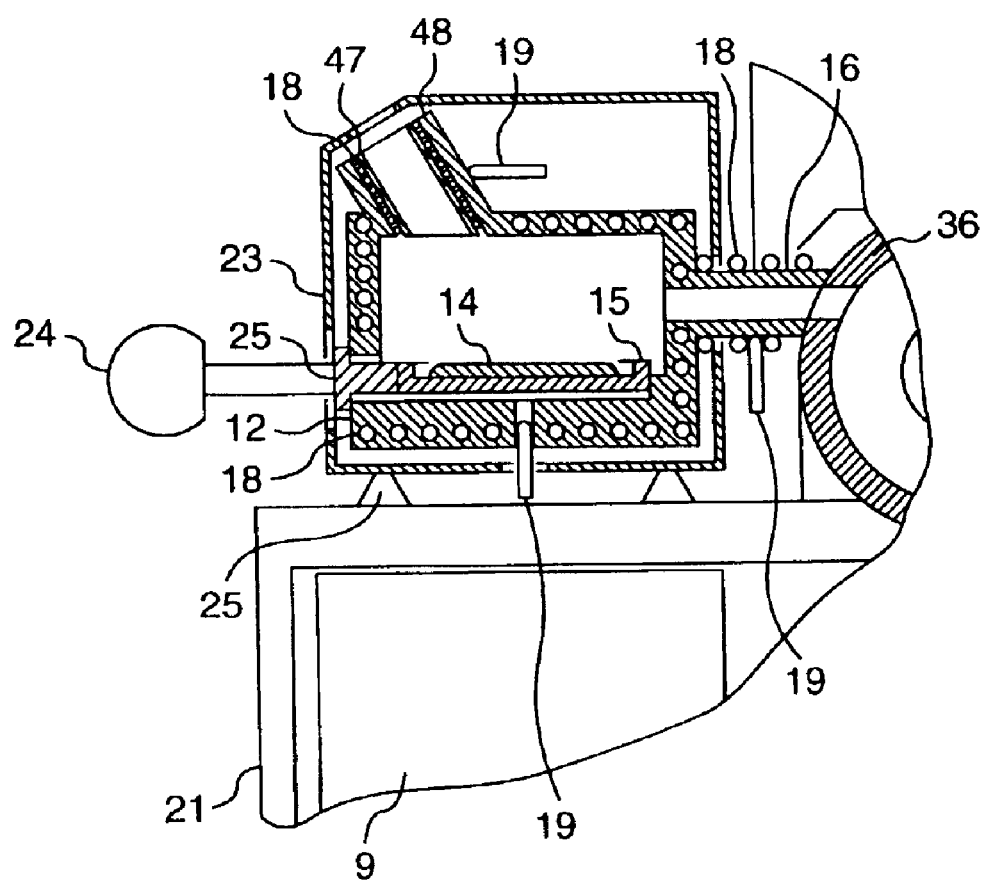
FIG. 14 is a partially sectioned side view illustrating the configuration of a dangerous substance detecting apparatus according to a fourth embodiment of the present invention.

FIG. 14 is a partially sectioned side view illustrating the configuration of a portable dangerous substance detecting apparatus according to a fourth embodiment of the present invention. When the x-, y- and z-axes are defined as shown in FIG. 2, the chamber 12 has a plane of symmetry parallel with the yz-plane. In FIG. 14, the cross section is taken along the plane of symmetry of the chamber 12, while the side view is taken from the positive direction of the x-axis. FIG. 14 illustrates the configuration of the dangerous substance detecting apparatus near the oven, which employs a heater for heating a gas instead of the halogen lamp in the first and second embodiments. Except for components associated with the heating of the test slip 14, the fourth embodiment is the same as the first and second embodiments in the remaining configuration, the power supply control for heating in the respective steps of the dangerous substance detection, and the determination on the identity of dangerous substances, so that description on such aspects is omitted.

In the fourth embodiment, the gas heating heater is disposed above the chamber 12. The gas heating heater, which is of a hollow type, has a heat source 18 disposed through a partition 47 from a gas flow path such that a gas passing through the hollow can be heated without being contaminated. A thermometer 19 is disposed on an outer shell 48 of the gas heating heater. The power supplied to the heat source 18 is controlled by the control unit 9 based on an output signal of the thermometer 19 disposed on the outer shell 48, so that the outer shell 48 can be heated to and maintained at a desired arbitrary temperature in a range of a room temperature to 300° C.

The gas heating heater is attached at an angle to the chamber 12 to provide a large viewing angle for the test slip 14 viewed from the hollow flow path of the gas heating heater. In addition, the gas heating heater is disposed on the opposite side to the introduction pipe 16 connected to the ion source unit 2 to irradiate the test slip 14 with a heated gas (air) produced by the gas heating heater without impeding the flow of air from the flow path of the gas heating heater, so that a sample (dangerous substances) stuck on the test slip 14 is heated in the chamber 12 for evaporation, and the evaporated sample is introduced into the ion source unit 2.

FIG. 15 is a graph showing a change over time in the strength of a signal indicative of trinitrotoluene having m/e=227, measured by irradiating an object under testing with heated air in the dangerous substance detecting apparatus according to the fourth embodiment of the present invention. As appreciated from the result shown in FIG. 15, by irradiating the test slip 14 with the air heated by the gas heating heater, the resulting signal indicative of an ion has a strength approximately four times as high as the result shown in FIG. 6 provided by the apparatus which comprises no special heating means other than the heat source 18 for heating the chamber 12 alone. Consequently, the apparatus according to the fourth embodiment can ensure the detection of dangerous substances with less erroneous reports.

(Fifth Embodiment)

Figure 16:
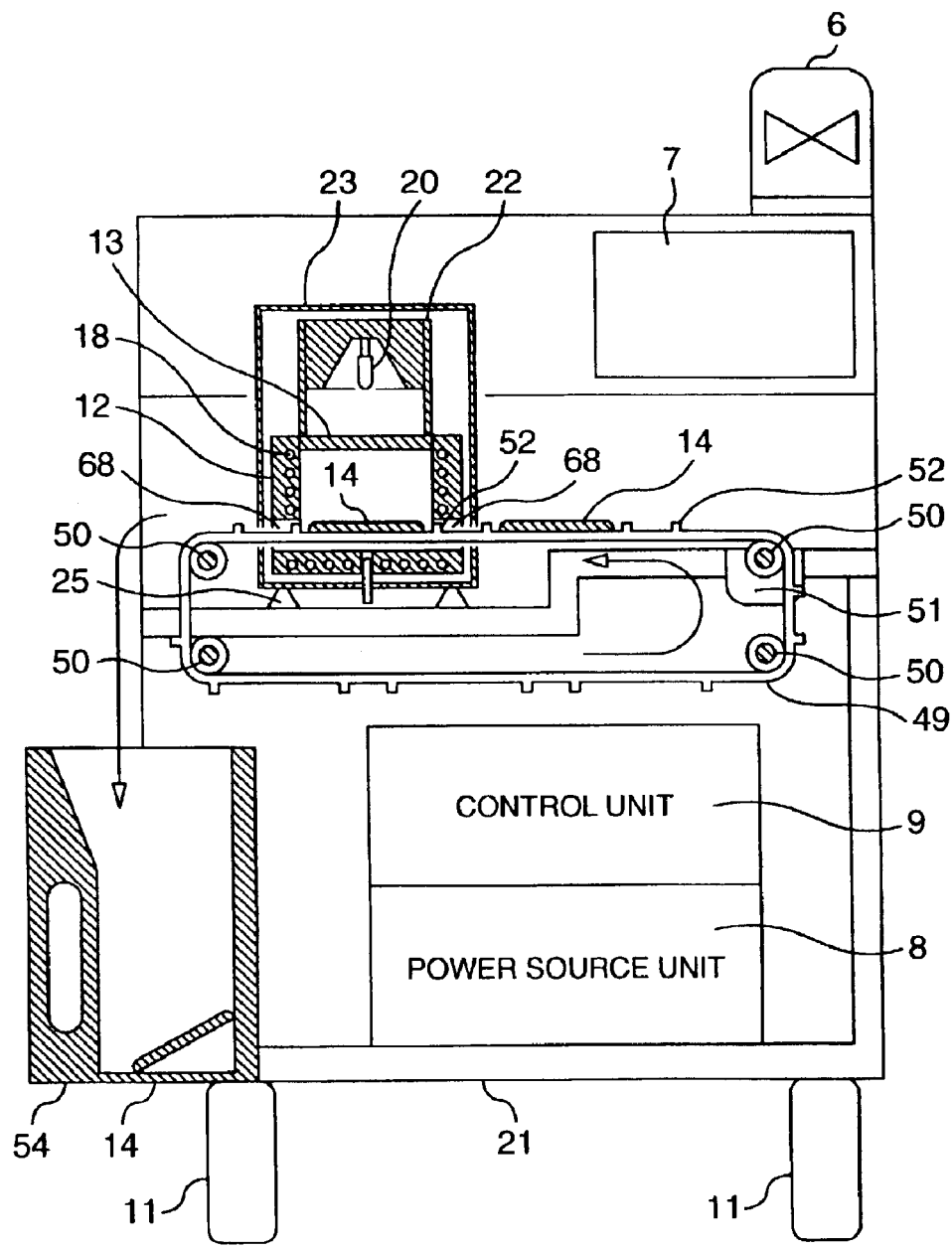
FIG. 16 is a partially sectioned side view illustrating the configuration of a dangerous substance detecting apparatus according to a fifth embodiment of the present invention.

FIG. 16 is a partially sectioned side view illustrating the configuration of a portable dangerous substance detecting apparatus according to a fifth embodiment of the present invention. When the x-, y- and z-axes are defined as shown in FIG. 2, the chamber 12 has a plane of symmetry parallel with the yz-plane. In FIG. 16, the cross section, which is perpendicular to the plane of symmetry of the chamber 12, is taken along a plane which passes through the center of a steel belt 49 in the width direction and is parallel with the xz-plane. The side view in turn is taken from the negative direction of the y-axis. FIG. 16 illustrates a modification to the configuration of the dangerous substance detecting apparatus according to the first embodiment, wherein a conveyer means comprised of a mesh steel belt 49 is arranged along an endless trajectory to convey a plurality of test slips 14, which serve as the wiping members, to the chamber 12 of the oven 1. Except for the components for conveying the wiping member into the chamber 12 of the oven 1, the fifth embodiment is the same as the first embodiment in the remaining configuration, the power supply control for heating in the respective steps of the dangerous substance detection, and the determination on the identification of dangerous substances, so that description on such aspects is omitted.

Rectangular openings 68 are formed through both side faces of the chamber 12 of the oven 1 such that the steel belt 49 passes through the openings 68. As illustrated in FIG. 16, the steel belt 49 forms an endless trajectory. Pulleys 50 hold the steel belt 49 for rotation relative to the housing 21 of the apparatus. A motor 51 is connected to the pulley 50 near a location at which the test slip 14 is placed on the steel belt 49. By rotating the motor 51, the steel belt 49 is driven in a direction indicated by the arrow. The steel belt 49 is formed with threshold plates 52 at equal intervals each for indicating the position at which the test slip 14 is placed.

The operator orients upward the surface of the test slip 14 on which the sample (particles) is stuck, and places the test slip 14 thus oriented at the position of the steel belt 49 indicated by the threshold plate 52. As the steel belt 49 is driven, the test slip 14 is carried into the chamber 12 through the opening 68. When a sensor (not shown) senses that the test slip 14 reaches a predetermined position within the chamber 12, the motor 51 is stopped to accordingly stop the steel belt 49. In this event, since the threshold plate 52 formed on the steel belt 49 is made to cover the opening 68 of the chamber 12, the sealability of the chamber 12 is maintained to some degree. Alternatively, the opening 68 may be completely closed by an open/close window, not shown.

After the steel belt 49 is stopped, the surface of the test slip 14, on which particles are stuck, is irradiated with infrared rays from the halogen lamp 20 to test for dangerous substance, in a manner similar to the aforementioned embodiments. After the completion of the test, the motor 51 is driven again to rotate the steel belt 49.

In the fifth embodiment, a dust box 54 is disposed on the exhaust side of the steel belt 49 for scavenging the test slip 14. After the completion of the test, the test slip 14 on the steel belt 49 is automatically dropped into the dust box 54 for recovery.

In the fifth embodiment described above, the operator can test the test slips 14 fed in sequence for dangerous substances stuck thereon through simple operations of placing the test slips 14 one by one on the steel belt 49. Because of the omission of the operations for introducing the test slip 14 into the chamber 12 and removing the test slip 14 from the chamber 12, the operator can concentrate attention on the handling of the test slip 14. In addition, the apparatus can be protected from damages due to failures in operating the oven 1 as well as from contaminations and the like.

The steel belt 49 can also be readily wiped or cleaned because the surface of the steel belt 49 on which the test slips 14 are placed is exposed external to the housing 21 of the apparatus. The steel belt 49 may be cleaned by a brush or the like which may be disposed somewhere below the steel belt 49 in the housing 21 for wiping the top face of the steel belt 49. In addition, the steel belt 49, loaded with no test slip 14, may be sequentially fed out for irradiating infrared rays from the halogen lamp 20 to the top face of the steel belt 49, on which the test slips 14 are placed, for heating, thereby efficiently removing impurities adsorbed on the steel belt 49 and residual dangerous substances adsorbed on the top face of the steel belt 49 on which the test slips are placed.

With the use of the endless steel belt 49, even if a particular threshold plate 52 of the steel belt 49 is heated during a test, the threshold plate 52 is spontaneously cooled down before the steel belt 49 is rotated to reach again the location at which another test slip 14 is placed on this threshold plate 52. Accordingly, even if a test slip 14 placed on the steel belt 49 includes the dangerous substance which exhibits the lowest evaporation temperature, the aforementioned erroneous report can be avoided because the evaporation of the dangerous substance can be avoided while the test slip 14 is being conveyed.

While the mesh steel belt 49 is employed in the fifth embodiment, the conveyer mechanism is not limited to the mesh steel belt 49. Alternatively, with a conveyer mechanism which employs a simple wide steel belt or a conveyer mechanism which employs a plurality of wound wires instead of the belt, the resulting dangerous substance detecting apparatus can provide similar advantages to those of the fifth embodiment, as should be taken as a matter of course.

(Sixth Embodiment)

Figure 17:
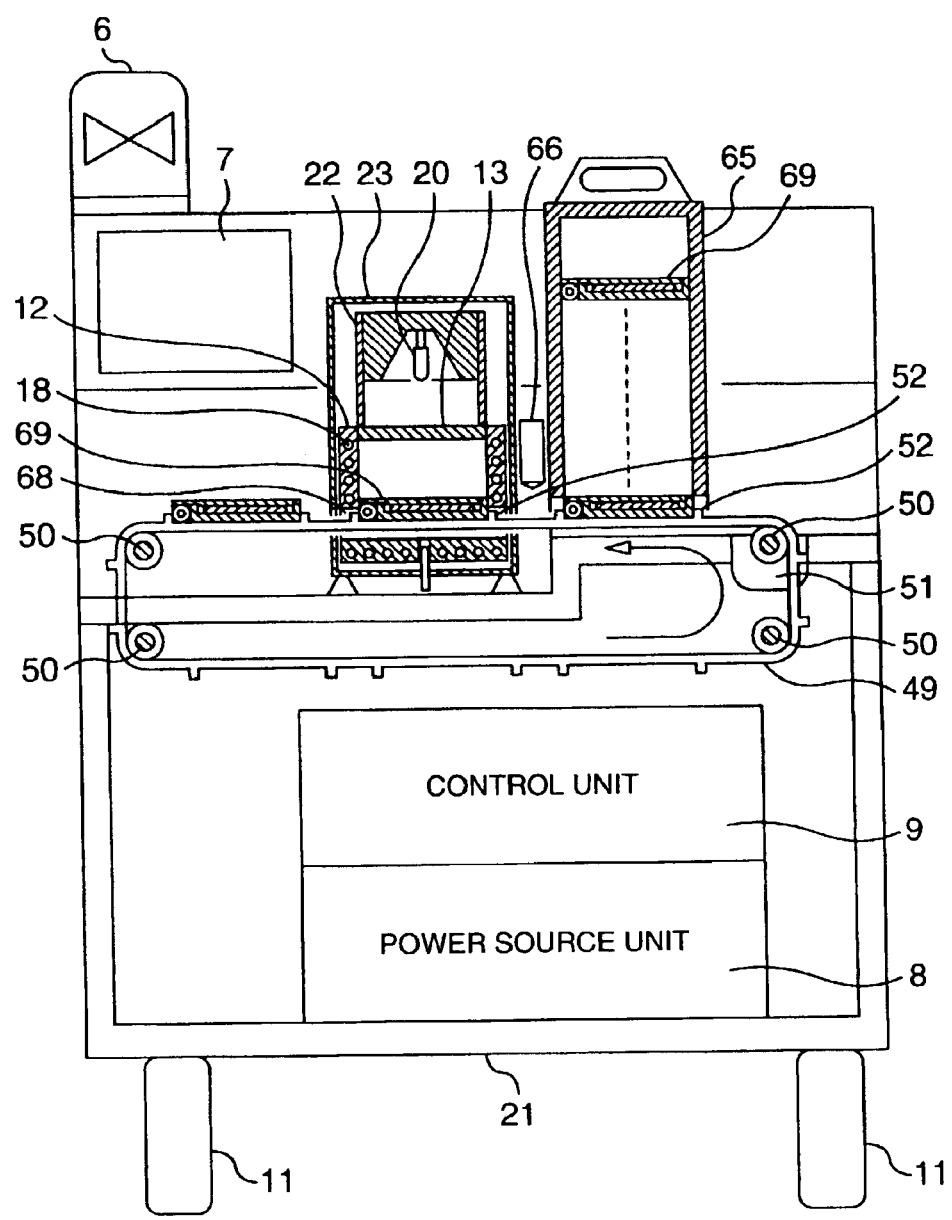
FIG. 17 is a partially sectioned side view illustrating the configuration of a dangerous substance detecting apparatus according to a sixth embodiment of the present invention.

FIG. 17 is a partially sectioned side view illustrating the configuration of a portable dangerous substance detecting apparatus according to a sixth embodiment of the present invention. When the x-, y- and z-axes are defined as shown in FIG. 2, the chamber 12 has a plane of symmetry parallel with the yz-plane. In FIG. 17, the cross-section, which is perpendicular to the plane of symmetry of the chamber 12, is taken along a plane which passes through the center of the steel belt 49 in the width direction and is parallel with the xz-plane, while the side view is taken from the negative direction of the y-axis.

Figure 18:
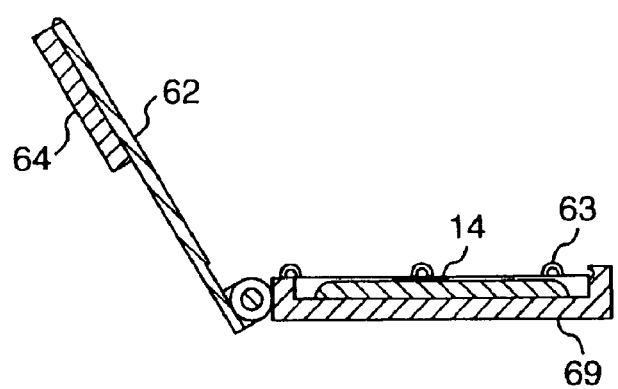
FIG. 18 is a cross-sectional view of a sample holder for use in the dangerous substance detecting apparatus according to the sixth embodiment of the present invention.

FIG. 18 is a cross-sectional view of a sample holder (holing member) 69, taken on the plane of symmetry, for use in the dangerous substance detecting apparatus according to the sixth embodiment of the present invention.

FIG. 17 illustrates a modification to the configuration of the fifth embodiment, wherein the dangerous substance detecting apparatus according to the sixth embodiment comprises a cassette 65 for accommodating a plurality of sample holders 69 each for holding the test slip 14 which serves as the wiping member, and a conveyer means for conveying the sample holders 69. The cassette 65 is disposed at a location corresponding to that location at which the operator places the test slip 14 on the steel belt 49 in the fifth embodiment.

In the configuration of the sixth embodiment, the alarm unit 6 and operation panel 7 are disposed at locations different from those in the fifth embodiment illustrated in FIG. 16.

After the operator has wiped an object under testing using a test slip 14, the test slip 14 is held in the sample holder 69 shown in FIG. 18. A movable mesh lid 62 of the sample holder 69 is opened to put the test slip 14 in the sample holder 69, so as to expose the surface which is stuck with particles, followed by closure of the lid 62. In this event, the lid 62 is not in contact with the wiping surface of the test slip 14 but only with the perimeter of the test slip 14. The sample holder 69 comprises a rotatable bearing 63 which comes into contact with another part of the apparatus to permit smooth relative movements of the sample holder 69.

The sample holder 69 comprises an identifying means 64 for identifying the sample holder 69, which permits the operator to identify from the test slip 14 the place where the sample was collected. While a bar code is used herein as the identifying means 64, an IC chip or the like may be used instead as the identifying means 64. The sample holder 69 which accommodates the test slip 14 is stored in the cassette 65 which is then carried to the dangerous substance detecting apparatus. The cassette 65 used in the sixth embodiment is capable of storing 12 sample holders 69. After storing the test slip 14 on which a sample is collected in the sample holder 68, the operator, holding the handle, carries the cassette 65 to the dangerous substance detecting apparatus.

The sixth embodiment also employs the belt conveyer means described in connection with FIG. 16 in the fifth embodiment. The cassette 65 is placed astride the steel belt 49. In this event, the height of the cassette 65 is set such that the sample holder 69 at the bottom of the cassette 65 is carried on the steel belt 49. As the threshold plate 52 disposed on the steel belt 49 urges the side face of the sample holder 69, the lowermost sample holder 69 alone is removed from the cassette 65. After the cassette 65 is fixed on the steel belt 49, the steel belt 49 is rotated in the direction indicted by the arrow, in a manner similar to the fifth embodiment. The sample holder 69 removed from the cassette 65 is conveyed to an identifying means reading unit 66 disposed in front of the chamber 12 which reads from the test slip 14 information such as the place in which the sample was collected. Then, the sample holder 69 is conveyed into the chamber 12. Subsequently, in a manner similar to the aforementioned embodiment, the test slip 14 stuck with the sample is heated to test whether or not a dangerous substance is present on the test slip 14. After the end of the test, the operator picks up the sample holder 69, conveyed out from the chamber 12, from the steel belt 49, and places the sample holder 69 in another cassette 65. In this event, the test slip 14 may be dropped into a dust box, not shown in FIG. 17, for recovery, in a similar configuration to that of the fifth embodiment.

According to the sixth embodiment, samples collected on a plurality of test slips 14 can be automatically tested at a site away from the dangerous substance detecting apparatus. For example, in an inspection on hand luggage in an airport, a passport of a hand luggage may be corresponded to the bar code on the sample holder 69, or the bar code of the cassette 65 may be corresponded to the ID of a cargo to identify a place in which the sample was collected in case a dangerous substance is detected from the test slip 14.

For simultaneously carrying a plurality of sample holders 69 accommodated in the cassette 65 into the chamber 12, the dangerous substance detecting apparatus may test the test slips 14 held in a plurality of sample holders 69 for samples stuck on the test slips 14. In this case, the bar code of the cassette 65 may be corresponded to the ID of a cargo to effectively identify a place in which the sample was collected in case a dangerous substance is detected from any test slip 14.

While the halogen lamp is used for heating in the fifth and sixth embodiments which employ the conveyer means, the conveyer means in the fifth and sixth embodiments may be applied to a dangerous substance detecting apparatus which comprises a rapid heating means other than the halogen lamp, for example, the gas heating heater in the fourth embodiment, or to a dangerous substance detecting apparatus which does not comprise a special rapid heating means such as the halogen lamp or the gas heating heater to provide similar advantages as those described above.

While the respective embodiments described above employ the quadrupole mass spectrography, an ion trap type mass spectrometer may be used instead. Also, since a sample (particles) wiped from the surface of an object under testing using the test slip can be heated by infrared rays for evaporation to generate the evaporated sample in a high concentration, the present invention can be applied to a known chemical emission type dangerous substance detecting apparatus which separates the vapor by gas chromatograph, reacts the separated vapor with an emission reagent to detect light emission, thereby testing the presence or absence of dangerous substances. The present invention can be further applied to a well known ion mobility type dangerous substance detecting apparatus which ionizes the vapor with a radioisotope within an ion source unit, introduces the ionized vapor into a drift tube to detect the mobility of the ions, thereby testing the presence or absence of dangerous substances.

According to the present invention, the dangerous substance detecting apparatus can improve the detection sensitivity for dangerous substances several tens of times as high without increasing the power consumption, thereby making it possible to sense dangerous substances without fail. Also, the dangerous substance detecting apparatus can ensure efficient detect of a variety of dangerous substances which have different evaporation temperatures. Further, with the addition of the conveyer means for automatically conveying the test slips, the dangerous substance detecting apparatus can automatically test the test slips in sequence without the need for special tools for handling the test slips. Furthermore, samples collected on a plurality of test slips can be tested in block at a site away from the dangerous substance detecting apparatus.

It should be understood that the dangerous substance detecting apparatus according to the present invention can be used in any of a portable form and a stationary form.

As appreciated from the foregoing description, the present invention provides a method and apparatus for detecting a dangerous substance which can detect dangerous substances at a high sensitivity with high operability.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A dangerous substance detecting apparatus comprising:
   a chamber for accommodating a wiping member so as to expose a surface on which a sample is stuck, said sample being collected from an object under testing through wiping, and for heating of said chamber for accommodating said wiping member;
   first heating means for heating said chamber through resistive heating;
   second heating means for heating the surface of said wiping member by irradiating the surface of said wiping member with infrared rays through an optical window from the outside of said chamber to evaporate said sample;
   control means for controlling supplying alternately and not simultaneously power to said first heating means and to said second heating means, wherein said control means controls the power so that the power for said first heating means is powered off while the power for said second heating means is powered on, and so that the power for said second heating means is supplied in steps, and in each of the steps, the power for said second heating means is powered on for several seconds for heating the surface of said wiping member at a different temperature to evaporate, at an atmospheric pressure, a different kind of dangerous substance included in said sample;
   an ion source unit for ionizing said evaporated sample;
   a mass analysis unit for performing a mass analysis on ions of said evaporated sample;
   storage means for storing a data base including mass spectrographic date on dangerous substances;
   a data processing unit for performing date processing for comparing said data base read from said storage means with the result of the mass analysis made on the ions of the evaporated sample in each step, wherein said data processing unit determines whether or not a detected signal indicative of an ion having a predetermined m/e value has a strength exceeding a predetermined threshold, where m is the mass number of ions, and e is the valence of the ions, for detecting and identifying different kinds of dangerous substances; and display means for displaying the result of the comparison, wherein said display means displays that a dangerous substance is included in said sample when the strength of the detected signal exceeds said threshold, wherein said apparatus determines the presence or absence of a dangerous substance included in said sample based on the result of the mass analysis on the ions of said evaporated sample, and detects and identifies different kinds of dangerous substances.

2. A dangerous substance detecting apparatus according to claim 1, comprising a holder member for holding said wiping member, said holder member being accommodated in said chamber.

3. A dangerous substance detecting apparatus according to claim 1, comprising conveyer means for conveying said wiping member into said chamber.

4. A dangerous substance detecting apparatus according to claim 1, comprising:
  a cassette for accommodating a plurality of holder members each for holding one of said wiping member; and
  conveyer means for conveying said holder members one by one from said cassette into said chamber.

5. A dangerous substance detecting apparatus according to claim 4, wherein said holder member and/or said cassette includes means for identifying said object under testing.

6. A dangerous substance detecting apparatus comprising:
  an atmospheric ion source unit having a corona discharge section;
  a wiping member receiver for receiving a wiping member which has a sample stuck thereon, said sample being collected from an object under testing through wiping;
  a housing configured to integrate said atmospheric ion source unit with said wiping member receiver;
  first heating means for heating said housing through resistive heating;
  second heating means for heating the surface of said wiping member by irradiating the surface of said wiping member with infrared rays through an optical window from the outside of said housing;
  control means for controlling supplying alternately and not simultaneously power to said first heating means and to said second heating means, wherein said control means controls the power so that the power for said first heating means is powered off while the power for said second heating means is powered on, and so that the power for said second heating means is supplied in steps, and in each of the steps, the power for said second heating means is powered on for several seconds for heating the surface of said wiping member at a different temperature to evaporate, at an atmospheric pressure, a different kind of dangerous substance included in said sample;
  means for applying a gas from said wiping member receiver to send said evaporated sample in said wiping member receiver to said corona discharge section;
  a mass analysis unit for performing a mass analysis on ions of said evaporated sample generated in said corona discharge;
  storage means for storing a data base including mass spectrographic data on dangerous substances;
  a data processing unit for performing data processing for comparing said data base read from said storage means with the result of the mass analysis made on the ions of the evaporated sample in each step, wherein said data processing unit determines whether or not a detected signal indicative of an ion having a predetermined m/e value has a strength exceeding a predetermined threshold, where m is the mass number of ions, and e is the valence of the ions, for detecting and identifying different kinds of dangerous substances; and
  display means for displaying the result of the comparison, wherein said display means displays that a dangerous substance is included in said sample when the strength of the detected signal exceeds said threshold,
  wherein said apparatus determines the presence or absence of a dangerous substance included in said sample based on the result of the mass analysis on the ions of said evaporated sample, and detects and identifies different kinds of dangerous substances.

7. A dangerous substance detecting apparatus according to claim 6, wherein said gas is applied to said corona discharge section from said wiping member receiver through a filter.

8. A dangerous substance detecting apparatus according to claim 6, wherein said wiping member includes a wiping section for wiping said sample from said object under testing, and a grip section.

9. A dangerous substance detecting apparatus according to claim 8, wherein said grip section includes means for identifying the surface of said wiping member on which said sample is stuck.

10. A dangerous substance detecting apparatus according to claim 6, wherein said wiping member receiver includes a movable side wall.

11. A dangerous substance detecting apparatus according to claim 6, wherein said wiping member receiver has an opening in an upper portion thereof, and said wiping member is inserted into said wiping member receiver through said opening.

12. A dangerous substance detecting apparatus according to claim 6, wherein said wiping member receiver has an opening in a lateral portion thereof, and said wiping member is inserted into said wiping member receiver through said opening.

13. A method for detecting a dangerous substance, comprising:
  heating a wiping member by first heating means to which power is supplied through resistive heating, wherein a sample is collected on a surface of said wiping member from an object under testing through wiping;
  heating the surface of said wiping member by second heating means which irradiates the surface of said wiping member with infrared rays through an optical window to evaporate said sample;
  controlling supplying alternately and not simultaneously power to said first heating means and to said second heating means, wherein said control means controls the power so that the power for said first heating means is powered off while the power for said second heating means is powered on, and so that the power for said second heating means is supplied in steps, and in each of the steps, the power for said second heating means is powered on for several seconds for heating the surface of said wiping member at a different temperature to evaporate, at an atmospheric pressure, a different kind of dangerous substance included in said sample;
  ionizing the evaporated sample;
  performing a mass analysis on ions of the evaporated sample;
  performing data processing for comparing a data base which includes mass spectrographic data on dangerous substances with the result of the mass analysis made on ions of the evaporated sample in each step, and determining whether or not a detected signal indicative of an ion having a predetermined m/e value has a strength exceeding a predetermined threshold, where m is the mass number of ions, and e is the valence of the ions, for sequentially detecting and identifying different kind of dangerous substances; and displaying the result of the comparison, wherein a dangerous substance included in said sample is displayed, when the strength of the detected signal exceeds said threshold, wherein said method determines the presence or absence of a dangerous substance included in said sample based on the result of the mass analysis on the ions of the evaporated sample.

14. A method for detecting a dangerous substance, comprising:

collecting a sample on a surface of a wiping member from an object under testing through wiping;

heating said wiping member by first heating means to which power is supplied through resistive heating, while supplying power to a second heating means is stopped, wherein a dangerous substance of a first kind in a sample is evaporated;

ionizing the dangerous substance of a first kind;

performing a mass analysis on ions of the dangerous substance of a first kind;

after stopping supplying the power to said first heating means, supplying a first power to said second heating means to irradiate the surface of the wiping member with infrared rays through an optical window to heat the surface of said wiping member to a first temperature to evaporate a dangerous substance of a second kind in said sample;

ionizing the dangerous substance of a second kind;

performing a mass analysis on ions of the dangerous substance of a second kind;

supplying a second power greater than the first power to said second heating means to heat the surface of said wiping member to a second temperature to evaporate a dangerous substance of a third kind in said sample;

ionizing the dangerous substance of a third kind in said sample;

performing a mass analysis on ions of the dangerous substance of a third kind;

performing data processing for comparing a data base which includes mass spectrographic data on different dangerous substances with the result of the mass analysis made on the ions of the dangerous substances of the first and second and third kinds, and for determining whether or not a detected signal indicative of an ion having a predetermined m/e value has a strength exceeding a predetermined threshold, where m is the mass number of ions, and e is the valence of the ions, for detecting and identifying the dangerous substances of first and second and third kinds; and displaying the result of the comparison, wherein dangerous substances included in said sample are displayed, when the strength of the detected signal exceeds said threshold, wherein said method determines the presence or absence of a dangerous substance included in said sample based on the result of the mass analysis on the ions of the dangerous substances of first and second and third kinds.

15. A substance detecting apparatus, comprising:

a chamber for accommodating a sample collection member so as to expose a surface on which a sample is provided, said sample being collected from an object under testing;

first heating means for heating said chamber;

second heating means for heating the surface of said sample collection member by irradiating the surface of said sample collection member with optical energy to evaporate said sample;

control means for controlling supplying power to said first heating means and to said second heating means, wherein said control means controls the power so that the power for said first heating means is powered off while the power for said second heating means is powered on, and so that the power for said second heating means is supplied in steps, and in each of the steps, the power for said second heating means is powered on for a predetermined time interval for heating the surface of said sample collection member at a different temperature to evaporate, at substantially atmospheric pressure, different substances of interest which may be included in said sample to produce an evaporated sample;

an ion source unit for ionizing said evaporated sample;

a mass analysis unit for performing a mass analysis on ions of said evaporated sample;

storage means for storing a data base including mass spectrographic data on substances of interest;

a data processing unit for performing data processing for comparing said data base read from said storage means with the result of the mass analysis made on the ions of the evaporated sample in each step, wherein said data processing unit determines whether or not a detected signal indicative of an ion having a predetermined m/e value has a strength exceeding a predetermined threshold, where m is the mass number of ions, and e is the valence of the ions, for detecting and identifying different kinds of substances of interest; and output means for making output available regarding the result of the comparison, wherein said output includes an indication that a substance of interest is included in said sample when the strength of the detected signal exceeds said threshold, wherein said apparatus determines the presence or absence of a substance of interest included in said sample based on the result of the mass analysis on the ions of said evaporated sample.

16. A substance detecting apparatus according to claim 15, comprising a holder member for holding said sample collection member, said holder member being accommodated in said chamber.

17. A substance detecting apparatus according to claim 15, comprising conveyer means for conveying said sample collection member into said chamber.

18. A substance detecting apparatus according to claim 15, comprising:

a cassette for accommodating a plurality of holder members each for holding said sample collection member, and conveyer means for conveying said holder members one by one from said cassette into said chamber.

19. A substance detecting apparatus according to claim 18, wherein ones of holder member and/or said cassette includes means for corresponding a respective said sample to a respective said object under testing.

20. A substance detecting apparatus comprising:
an atmospheric ion source unit having a corona discharge section;
a sample collection member receiver for receiving a sample collection member which has a sample provided thereon, said sample being collected from an object under testing;
a housing configured to integrate said atmospheric ion source unit with said sample collection member receiver;
first heating means for heating said housing;
second heating means for heating the surface of said sample collection member by irradiating the surface of said sample collection member with optical energy;
control means for controlling supplying power to said first heating means and to said second heating means, wherein said control means controls the power so that the power for said first heating means is powered off while the power for said second heating means is powered on, and so that the power for said second heating means is supplied in steps, and in each of the steps, the power for said second heating means is powered on for a predetermined time interval for heating the surface of said sample collection member at a different temperature to evaporate, at substantially atmospheric pressure, different kinds of substances of interest which may be included in said sample to produce an evaporated sample;
means for applying a gas from said sample collection member receiver to send said evaporated sample in said sample collection member receiver to said corona discharge section;
a mass analysis unit for performing a mass analysis on ions of said evaporated sample generated in said corona discharge:
storage means for storing a data base including mass spectrographic data on substances of interest;
a data processing unit for performing data processing for comparing said data base read from said storage means with the result of the mass analysis made on the ions of the evaporated sample in each step, wherein said data processing unit determines whether or not a detected signal indicative of an ion having a predetermined m/e value has a strength exceeding a predetermined threshold, where m is the mass number of ions, and e is the valence of the ions, for detecting and identifying different kinds of substances of interest; and
output means for making output available regarding the result of the comparison, wherein said output includes an indication that a substance of interest is included in said sample when the strength of the detected signal exceeds said threshold,
wherein said apparatus determines the presence or absence of a substance of interest included in said sample based on the result of the mass analysis on the ions of said evaporated sample.

21. A substance detecting apparatus according to claim 20, wherein said gas is applied to said corona discharge section from said sample collection member receiver through a filter.

22. A substance detecting apparatus according to claim 20, wherein said sample collection member includes a sample collection section for collecting said sample from said object under testing, and a grip section.

23. A substance detecting apparatus according to claim 22, wherein said grip section includes means for identifying the surface of said sample collection member on which said sample is collected.

24. A substance detecting apparatus according to claim 20, wherein said sample collection member receiver includes a movable side wall.

25. A substance detecting apparatus according to claim 20, wherein said sample collection member receiver has an opening in an upper portion thereof, and said sample collection member is inserted into said sample collection member receiver through said opening.

26. A substance detecting apparatus according to claim 20, wherein said sample collection member receiver has an opening in a lateral portion thereof, and said sample collection member is inserted into said sample collection member receiver through said opening.

27. A method for detecting a substance, comprising:
heating a sample collection member by first heating means to which power is supplied to a heating unit, wherein a sample is provided on a surface of said sample collection member from an object under testing;
heating the surface of said sample collection member by second heating means which irradiates the surface of said sample collection member with optical energy to evaporate said sample;
controlling supplying power to said first heating means and to said second heating means, wherein said control means controls the power so that the power for said first heating means is powered off while the power for said second heating means is powered on, and so that the power for said second heating means is supplied in steps, and in each step, the power for said second heating means is powered on for a predetermined time interval for heating the surface of said sample collection member at a different temperature to evaporate, at substantially atmospheric pressure, a different kind of substance of interest which may be included in said sample to produce an evaporated sample;
ionizing the evaporated sample in each step;
performing a mass analysis on ions of the evaporated sample in each step;
performing data processing for comparing a data base which includes mass spectrographic data on substances of interest with the result of the mass analysis made on ions of the evaporated sample in each step, and determining whether or not a detected signal indicative of an ion having a predetermined m/e value has a strength exceeding a predetermined threshold, where m is the mass number of ions, and e is the valence of the ions, for sequentially detecting and identifying different kind of substances of interest; and
making output available regarding the result of the comparison, wherein an indication of any substance of interest is included in said output, when the strength of the detected signal exceeds said threshold,
wherein said method determines the presence or absence of a substance of interest included in said sample based on the result of the mass analysis on the ions of the evaporated sample.

28. A method for detecting a substance, comprising:
heating a sample collection member by first heating means to which power is supplied through a heating unit, while supplying power to a second heating means is stopped, wherein any substance of interest of a first kind in a sample is evaporated to produce a first evaporated sample;
ionizing the substance of interest of a first kind in said first evaporated sample to produce a first ionized sample;

performing a mass analysis on ions of the first ionized sample;

after stopping supplying the power to said first heating means, supplying a first power to said second heating means to heat the surface of said sample collection member to a first temperature to evaporate any substance of interest of a second kind in said sample to produce a second evaporated sample;

ionizing the substance of interest of the second kind in said second evaporated sample to produce a second ionized sample;

performing a mass analysis on ions of the second ionized sample;

supplying a second power greater than the first power to said second heating means to heat the surface of said sample collection member to a second temperature to evaporate any substance of interest of a third kind in said sample to produce a third evaporated sample;

ionizing the substance of interest of the third kind in said third evaporated sample to produce a third ionized sample;

performing a mass analysis on ions of the third ionized sample;

performing data processing for comparing a data base which includes mass spectrographic data on different substances of interest with the result of the mass analysis made on the ions of the substances of interest of the first, second and third kinds in said first, second and third ionized samples, and for determining whether or not a detected signal indicative of an ion having a predetermined m/e value has a strength exceeding a predetermined threshold, where m is the mass number of ions, and e is the valence of the ions, for detecting and identifying substances of interest of the first, second and third kinds; and making output available regarding the result of the comparison, wherein an indication of any substances of interest included in said sample is included in said output, when the strength of the detected signal exceeds said threshold, wherein said method determines the presence or absence of a substance of interest included in said sample based on the result of the mass analysis on the ions of the first, second and third ionized samples.

\* \* \* \* \*